US007285094B2

(12) United States Patent
Nohara et al.

(10) Patent No.: US 7,285,094 B2
(45) Date of Patent: Oct. 23, 2007

(54) 3D ULTRASONIC IMAGING APPARATUS AND METHOD

(76) Inventors: Timothy J. Nohara, 71 Millbridge Cr., Fonthill, Ontario (CA) L0S 1E1; Peter Weber, 6 Briar Lane, Dundas, Ontario (CA) L9H 6E8; Richard Bernardi, 440 Woodcrest Rd., Wayne, PA (US) 19087

( * ) Notice: Subject to any disclaimer, the term of this patent is extended or adjusted under 35 U.S.C. 154(b) by 0 days.

(21) Appl. No.: 10/353,152

(22) Filed: Jan. 28, 2003

(65) Prior Publication Data

US 2003/0163046 A1 Aug. 28, 2003

Related U.S. Application Data

(63) Continuation of application No. 60/352,969, filed on Jan. 30, 2002.

(51) Int. Cl.
*A61B 8/00* (2006.01)

(52) U.S. Cl. ...................................................... 600/447

(58) Field of Classification Search ................ 600/443, 600/447, 454–456; 128/916; 73/625–626; 367/7, 11, 121–123, 138
See application file for complete search history.

(56) References Cited

U.S. PATENT DOCUMENTS

| | | | |
|---|---|---|---|
| 3,552,382 | A | 1/1971 | Mount |
| 3,805,596 | A | 4/1974 | Klahr |
| 3,927,662 | A | 12/1975 | Ziedonis |
| 4,048,616 | A | 9/1977 | Hart et al. |
| 4,149,420 | A | 4/1979 | Hutchison et al. |
| 4,315,514 | A | 2/1982 | Drewes et al. |
| 4,395,909 | A | 8/1983 | Steinberg et al. |
| 4,434,661 | A | 3/1984 | Miwa et al. |
| 4,446,740 | A | 5/1984 | Wilson et al. |
| 4,623,219 | A | 11/1986 | Trias |
| 4,646,158 | A | 2/1987 | Ohno et al. |
| 4,757,820 | A | 7/1988 | Itoh |
| 4,771,786 | A | 9/1988 | Iinuma |
| 4,819,649 | A | 4/1989 | Rogers et al. |
| 4,991,604 | A | 2/1991 | Wurster et al. |

(Continued)

OTHER PUBLICATIONS

"Elevation Performance of 1.25D and 1.5D Transducer Arrays," Wildes, D.G. et al., IEEE Transactions on Ultrasound, Ferroelectronics and Frequency Control, vol. 44, No. 5, Sep. 1997, pp. 1027-1036.

(Continued)

*Primary Examiner*—Francis J. Jaworski
(74) *Attorney, Agent, or Firm*—R. Neil Sudol; Henry D. Coleman; William J. Sapone

(57) ABSTRACT

A probe for electronic volume data acquisition using ultrasound incorporates a plurality of transducer elements arranged in a two dimensional array having an azimuth direction and an elevation direction. The transducer elements have a first element size in the azimuth dimension and a second element size in the elevation dimension. At least one of the first and second element sizes is at least twice a characteristic wavelength of a waveform used to drive the array of transducer elements, where the characteristic wavelength is defined as the wavelength corresponding to a center frequency of the waveform. Image data is generated in a scanning process using a CAC-BF technique in an azimuth dimension and/or an elevation dimension, to form an ultrasound image line, image plane, or image data cube.

36 Claims, 7 Drawing Sheets

48 Transducer Array
50
52 Signal Generator
56 Switching Network
54 Control Unit
58
90
60 Digitizer
62 Coarse Beamformer
64 Range Filter
66 Fine Beamformer
86 Image Generator
88 Memory
84 Video Monitor

U.S. PATENT DOCUMENTS 5,078,143 A 1/1992 Okazaki et al.
5,091,893 A 2/1992 Smith et al.
5,099,459 A 3/1992 Smith
5,099,848 A 3/1992 Parker et al.
5,113,706 A 5/1992 Pittaro
5,135,001 A 8/1992 Sinofsky et al.
5,152,294 A 10/1992 Mochizuki et al.
5,163,436 A 11/1992 Saitoh et al.
5,167,231 A 12/1992 Matsui
5,203,336 A 4/1993 Iida et al.
5,235,986 A 8/1993 Maslak et al.
5,375,470 A 12/1994 Matsushime et al.
5,391,140 A 2/1995 Schaetzle et al.
5,394,877 A 3/1995 Orr et al.
5,417,215 A 5/1995 Evans et al.
5,435,311 A 7/1995 Unemura et al.
5,448,994 A 9/1995 Iinuma
5,488,952 A 2/1996 Schoolman
5,490,512 A * 2/1996 Kwon et al. ................ 600/447
5,497,776 A 3/1996 Yamazaki et al.
5,526,815 A 6/1996 Granz et al.
5,611,343 A 3/1997 Wilson
5,611,345 A 3/1997 Hibbeln
5,619,999 A 4/1997 Von Behren et al.
5,666,953 A * 9/1997 Wilk .......................... 600/407
5,667,373 A 9/1997 Wright et al.
5,677,491 A * 10/1997 Ishrak et al. .................. 73/641
5,680,863 A 10/1997 Hossack et al.
5,682,895 A 11/1997 Ishiguro
5,793,701 A * 8/1998 Wright et al. .................. 367/7
5,806,521 A 9/1998 Morimoto et al.
5,817,019 A 10/1998 Kawashima
5,871,446 A * 2/1999 Wilk .......................... 600/407
5,976,089 A * 11/1999 Clark ......................... 600/447
5,984,882 A 11/1999 Rosenschein et al.
5,997,479 A 12/1999 Savord et al.
6,007,489 A 12/1999 Yost et al.
6,023,632 A * 2/2000 Wilk .......................... 600/407
6,106,463 A 8/2000 Wilk
6,106,471 A 8/2000 Wiesauer et al.
6,129,672 A 10/2000 Seward et al.
6,135,960 A 10/2000 Holmberg
6,155,978 A 12/2000 Cline et al.
6,159,153 A 12/2000 Dubberstein et al.
6,183,419 B1 * 2/2001 Wildes ....................... 600/447
6,213,947 B1 4/2001 Phillips
6,213,948 B1 4/2001 Barthe et al.
6,238,346 B1 * 5/2001 Mason ....................... 600/459
6,276,211 B1 8/2001 Smith
6,319,201 B1 * 11/2001 Wilk .......................... 600/437
6,419,633 B1 7/2002 Robinson et al.
6,482,160 B1 11/2002 Stergiopoulos et al.
6,503,204 B1 1/2003 Sumanaweera
6,692,439 B1 * 2/2004 Walker et al. .............. 600/443

OTHER PUBLICATIONS

"Elevation Beamforming Performance of a 1.75D Array," Guo, Puyun et al., IEEE Ultrasound, Ferroelectronics and Frequency Control, 2001.

Li, P. et al "Phase Aberration Correction on Two-Dimensional Conformal Arrays", IEEE Trans UFFC V42#1 Jan. 1995 pp. 73-82.

* cited by examiner

PRIOR ART

46a2
46b2
75'
72c
72b
72a
46a1
73'
70
72d
72d
46b1
73
75
73
Legend
voxel grid point
subaperture 1 beam signal sample point
subaperture 2 beam signal sample point 42
46a1
46a2
46ai
46b1
46b2
46bj
46n1
46n2
46nk
44a
44b
44n

3D ULTRASONIC IMAGING APPARATUS AND METHOD

FIELD OF INVENTION

This invention relates to ultrasound imaging systems. More particularly, this invention relates to methods and devices for three-dimensional image acquisition. The devices and methods are also suitable for 2D and 4D ultrasound systems. The invention is particularly, but not exclusively, useful for medical diagnoses and treatment. The devices and methods of the present invention are useful components of practical high-quality real-time 3D ultrasound systems with fully electronic volume data acquisition.

BACKGROUND OF THE INVENTION

Two-dimensional (2D) ultrasonic probes are necessary to support three-dimensional (3D) electronic, volume data acquisition for many clinical applications. State-of-the-art one-dimensional (1D and 1.5D) probes which electronically scan only in azimuth provide the 2D ultrasound images (azimuth and range) which are commonly used today. 2D probes scan electronically in elevation as well as azimuth, to provide a three dimensional data cube (azimuth, elevation and range) which can be processed using image processing software to produce a variety of image formats. These formats include conventional planar images, planar images at arbitrary scan planes, as well as representations such as surface rendering and orthographic presentations. Four-dimensional (4D) representations include 3D animations where the 3D rendering is updated in time.

Two-dimensional sensors are employed in other imaging modalities such as CT-scanners, and in other fields such as radar; and hence are well understood conceptually. Practical difficulties arise with the ultrasound modality due to the small, elemental feature size (fractions of a mm) and the large number of channels typically needed. These difficulties have stalled the introduction of fully electronic, 2D, ultrasonic probes.

Ultrasound systems today make use of a variety of 1D and 1.5D ultrasonic arrays. A 1D array has a fixed elevation aperture which is focussed at a fixed range, and is usually realized with a mechanical lens of sorts. A 1.5D array, on the other hand, has a variable elevation aperture, shading and focussing, but they are symmetric about the centerline of the array.

1D array transducers contain several tens or even hundreds of elements typically arranged linearly. The transducer elements 10, 12 may be arranged on a straight line (linear array) or a curved line (curved linear array or simply curved array) as shown in FIGS. 1A and 1B, respectively. The operation of a linear array or curved array are similar, the main difference being that the image expands with range (depth) for the curved array. A typical linear or curved array could have anywhere from 64 to 512 (or more) elements, depending on the cost and the application. The azimuthal spacing of elements is typically between half a wavelength and one wavelength. The elemental size in the elevation dimension is much larger, typically tens of wavelengths. The operating frequency is typically somewhere between 2 MHz to 20 MHz, depending on the clinical application.

Let's consider an example, where a 7.5 MHz curved array of the type shown in FIG. 1B has 256 transducer elements 12 in azimuth spaced by one wavelength; and the dimension of an element in elevation is, say, 40 wavelengths. At 7.5 MHz, the wavelength, $\lambda$, in tissue is about 0.2 mm. Therefore, the array spans about 51 mm in azimuth and 8 mm in elevation.

A narrow beam is created in the azimuth dimension by focussing the transmitted and receive energy along a particular beam or scan line 14, 16, as illustrated in FIG. 2A and FIG. 2B. Scanning is performed in azimuth (i.e. in a single elevation plane) using one of two schemes, sequential scanning or phased-array scanning. With sequential scanning, any given beam line is offset from all of the other beam lines in the azimuth direction. If the array is linear (rather than curved), the beam lines 16, 18 are parallel to one another (FIG. 3A). With reference to FIG. 2B, the central beam line 16 that is illustrated is shifted (offset) to the left or right with different offsets 20 to create a set of beam lines 22 that spans the region or volume to be imaged, as illustrated in FIG. 3A. Phased-array scanning, on the other hand, is achieved by rotating the central beam line 24 illustrated in FIG. 3B in azimuth, to the left and to the right, by a set of angular offsets 26. The beam lines 28 of the resulting set 30 of beam lines intersect at a common apex 32 (which may actually occur behind the array), and separate from each other as a function of range, as illustrated in FIG. 3B.

Premium probes generally employ wideband waveforms to achieve the fine resolutions needed in range. As a result, beamforming is done by adjusting time delays (in the narrowband waveform case, phases are adjusted rather than time delays) at each element used on transmit and receive. For a given pulse, a focal point is set along the range dimension. Appropriate time delays are used on the elements involved in transmission, so that their respective acoustic energy arrives at the specified focal range, along the specified beam line, at the same time. As a result, the waveform is said to be focussed at this point. On receive, time delays are dynamically applied to the elements involved in reception, to focus the received energy at each range.

Generally speaking, focussing is needed only in the near field of the array, where the ultrasound wave cannot be assumed to be planar, as it is in the far field. If one looks closely at the effect of this focussing operation in the azimuth and elevation spatial dimensions, one notices a difference. In azimuth, numerous transducer elements are available, each with a respective time delay to adjust dynamically with range on receive. The result is the azimuth resolution of the beam can be generally maintained uniformly with range as illustrated in FIG. 2A for a 1D linear array. There are no delays to adjust in elevation, however. As a result, a typical, fixed, lens-like beam pattern results in the elevation dimension, with the best elevation resolution occurring at the transmit focal point (in range), and with a degradation of the elevation resolution as one moves away from this focal point in range. This effect is also illustrated in FIG. 2A. The image plane thickness (i.e. in the elevation dimension) in effect varies with range for a 1D linear array.

The 1.5D array provides a solution to the image thickness problem, and therefore produces higher-quality, planar images than the 1D array (Wildes, D. G., et al., "Elevation Performance of 1.25D and 1.5D Transducer Arrays", IEEE Transactions on Ultrasound, Ferroelectronics and Frequency Control, Vol. 44, No. 5, September 1997, pp.1027 to 1036). By using multiple rows of elements in the elevation dimension, as illustrated in FIG. 2B, multiple elevation lenses can be effected, each focussed at a different focal range. This is achieved by varying the time delays (through switching or otherwise) applied to the elevation elements while the acoustic signals are being received. In addition, a lens is typically used in the elevation dimension to help control the elevation focus. The net effect is that the elevation thickness (resolution) is maintained with range, thereby improving image quality. This is illustrated in FIG. 2B.

In a typical 1.5D array, each element might be $\lambda \times 4\lambda$ (i.e. azimuth by elevation) in dimension. For an array with 128 elements per row and 8 rows of elements, the elevation dimension is $32\lambda$ or 6.4 mm and the azimuth dimension is $128\lambda$ or 25.6 mm at 7.5 MHz.

Consider the linear 1.5D array shown in FIG. 3A, containing 256 elements 34 in azimuth. Now 128 sequential beams 18 are typically used to form a rectangular, azimuthal image plane by scanning in azimuth as illustrated in the figure. Typical transducer dimensions for this state-of-the-art array are also indicated. (Note: only 16 columns of elements 34 are shown in FIG. 3A, for simplicity, where in fact, 256 elements are represented in the azimuth dimension).

A state-of-the-art array with $\lambda/2$ spacing in azimuth to support phased-array scanning is illustrated in FIG. 3B. This type of array produces pie-shaped images in contrast to the rectangular images produced using sequential arrays.

Unlike 1.5D arrays which are commonly found in premium ultrasound systems, 1.75D arrays are not yet in use in commercial systems (Puyun Guo, Shikui Yan and Quing Zhu, "Elevation Beamforming Performance of a 1.75D array", IEEE 2001 Ultrasound, Ferroelectronics and Frequency Control Conference). 1.75D arrays are like 1.5D arrays, except there is no symmetry constraint. As a result, it is possible to provide a little bit of elevation steering. However, due to the large element size in elevation (several wavelengths), grating lobes become serious if the electronic scanning is significant (Puyun Guo, Shikui Yan and Quing Zhu, "Elevation Beamforming Performance of a 1.75D array", IEEE 2001 Ultrasound, Ferroelectronics and Frequency Control Conference).

Interest in 3D Ultrasound is growing and all major ultrasound companies are paying attention. There are two ways that scanning is currently performed: sequential scanning and phased array scanning. It is common knowledge to those skilled in the art that if one conventionally-extends a 1D phased array (typically with $\lambda/2$ element spacing) to two dimensions (of equal size), or a 1D sequential array (typically with $\lambda$ element spacing) to two dimensions, then data cubes could be acquired by 2D scanning, and the fine (e.g. an F number of 2, denoted herein as F/2) azimuth resolution currently available extends to elevation as well. Two fundamental difficulties, however, arise:

1. the cost is prohibitive;
2. the frame-time to acquire a 3D volume is far greater than the time it takes to acquire a 2D image.

Consider extending a linear array with 256 elements (maximum of 128 used on receive) to two dimensions. The number of elements increases to 256×256=65,536. Transducer design/fabrication is very difficult, if not impossible, today. The number of receiver channels would also increase by a factor of 128 in order to provide the same resolution in both dimensions, all else being equal, while not increasing the number of shots (and hence acquisition time) needed per vector. Since system cost is proportional to the number of channels, the resulting cost is unaffordable.

Finally, it takes longer to acquire the data cube (as compared to the tens of milliseconds needed to acquire a conventional 2D image plane) since there are many more beams needed to interrogate the volume. At least 128×128=16,384 beams are needed, for each transmit focal range, with about 100 μs two-way time needed for each shot (this assumes a 10 kHz firing rate and a 7 cm depth needed). For two focal ranges, this implies an acquisition time of 3.2 seconds, assuming the number of channels available equals the number of elements used in the beamformer.

The aforementioned difficulties require practical tradeoffs and novel solutions if 2D arrays supporting 3D electronic, volume data acquisition are to be an affordable reality.

Additional Prior Art

Many engineers have attempted to solve the aforementioned difficulties in order to help make 3D ultrasound imaging an affordable reality. Some of the more relevant approaches with respect to the current inventions are discussed below.

As a result of the complexities associated with 2D electronic scanning, some engineers have proposed the use of mechanical scanning in the elevation dimension. That is, a conventional, 1D linear array is used to provide the conventional, B- or C-mode, range-azimuth, planar image; but it is moved up and down quickly using mechanical means such as a motor, to acquire successive planar images at a set of elevation positions. In U.S. Pat. No. 6,106,471 "Procedure for an Examination of Objects by the Means of Ultrasound Waves", Wiesauer, Fosodeder and Gritzky describe such an approach. The mechanical movement in the elevation dimension is done automatically and continuously using a motor in the 2D probe housing. As focussing scan lines requires precise, a priori knowledge of the location of the 1D array elements with time, the quality of 2D and 3D imagery produced using this approach is limited by the accuracy of the mechanical movements in the elevation dimension.

In Ultrasonic Blanket with CAC and SCA Patent Application, U.S. Ser. No. 09/514,928, filed Feb. 28, 2000, 3D volume data acquisition and focussing of beams using active transducers is described. A singular, rigid carrier structure constructed using scalar transducer elements arranged in the likeness of an array is disclosed. Signal transmission apertures and data gathering apertures are formed and used to electronically scan desired regions and electronically acquire 3D volumetric data; where coherent aperture combining (CAC) is used to combine the structural data from multiple data gathering apertures, thereby increasing the size of the effective data gathering apertures employed, and thereby increasing image resolution. Both monostatic (on pulse one, transmit and receive out of aperture one, on pulse two, transmit and receive out of aperture two) and bistatic (transmit from one aperture and receive simultaneously on two or more apertures) operations are disclosed. Also disclosed is the use of 1.5D and 1.75D array technology to form a 2D array and effectuate volume data acquisition by scanning in azimuth and elevation.

In U.S. Pat. No. 6,482,160 "High Resolution 3D Ultrasound Imaging System Deploying a Multidimensional Array of Sensors and Method for Multidimensional Beamforming Sensor Signals", Stergiopoulos and Dhanantwari describe an adaptive beamforming method which can be used to process sensor signals received on a 2D array of sensors in order to generate a high resolution, 2D beam response for each of a set of beam directions defined by azimuth-elevation angle pairs. The method described in the specification is applicable to the case where the imaged object is in the far-field of the 2D array of sensors, and relates only to processing techniques to be used on receive. It is assumed that a single, low-gain, transmit sensor (e.g. an omni-directional transducer element) is located away from the 2D array of sensors and illuminates the entire region being imaged, causing the ultrasound energy to reflect from the object towards the receiving array. The inventors exploit adaptive beamforming algorithms to increase the spatial resolution otherwise unobtainable from the receive array, had conventional, linear beamforming techniques such as the discrete Fourier transform been used. In theory, adaptive algorithms can estimate the noise process competing with the desired signal associated with each beam, and use this information to adapt the receive beam so as to better suppress the noise. Adaptive and linear beamforming techniques are well known to those skilled in the art. The inventors acknowledge that if the assumed noise characteristics are inaccurate, performance of the adaptive beamformer will degrade significantly and may even result in cancellation of the desired signal. Furthermore, implementing adaptive algorithms directly on the full array of sensor data requires very significant computational resources; and convergence of the adaptive solution requires significant training data. To mitigate these practical difficulties, the inventors propose a partially adaptive beamformer which reduces the number of adaptive degrees of freedom (DOF) by preprocessing the array sensor data using conventional Fourier beamforming. The partially adaptive beamformer, for the case of a 2D array, begins by dividing the array into smaller subapertures, each of which is a 2D array. For each subaperture, a 2D conventional beamformer is implemented, which, for computational efficiency, is organized as a cascade of two 1D beamformers. For example, each row of the subaperture's sensor data would be processed using a 1D azimuth Fourier beamformer; and then the resulting column of azimuth-processed data would be operated on by a 1D elevation Fourier beamformer. This cascaded approach, known to those skilled in the art, only applies for the case of far-field imaging. Finally, adaptive beamforming is performed on the resulting, conventionally-beamformed subaperture signals, by adaptively processing those respective subaperture signals which were conventionally-beamformed to the same azimuth-elevation angle direction.

In U.S. Pat. No. 6,419,633 "2D Ultrasonic Transducer Array for Two Dimensional and Three Dimensional Imaging", A. Robinson, B. Robinson and Detmer describe a particular implementation of an electronic 2D array. The inventors disclose an electronic 2D transducer array that can be configured or switched to provide both 2D arrays and 1D arrays for 3D and 2D imaging, respectively. A variety of particular element switching and summing circuits are disclosed to combine rows and columns of elements as needed for each supported array configuration. By these designs, the inventors intend to limit the total number of signal leads coming out of their transducer (and by implication, the number of digital receiver channels in the ultrasound system). This objective is achieved primarily by using a sparse 2D array on receive, with admitted negative implications on array sensitivity and grating lobes. In the example, 19-by-19 2D transducer array used for illustration, only 100 signal leads are needed to support the sparse 2D array configuration, rather than 361 leads if all elements were used. They also intend that 2D image quality is not degraded, as compared to conventional 1D arrays which are optimized for this purpose. This objective is met by configuring the 2D transducer array as a fully populated, 1D array.

In U.S. Pat. No. 6,238,346 "System and Method Employing Two-dimensional Ultrasound Array for Wide Field of View Imaging", inventor Mason discloses a 2D rectangular transducer array which scans an elongated sector volume using fewer transducer elements than in prior art systems, while avoiding sidelobe anomalies. The switching circuitry forms a number of small subarrays, where each subarray spans the entire elevation dimension and includes a contiguous subset of azimuth elements. Each subarray is shifted from the next in azimuth by one element. The 2D array provides phased-array scanning in the shorter elevation dimension using all of the elements in each subarray. Conventional arrays, on the other hand, perform phased-array scanning on the longer azimuth dimension. The disclosed 2D array scans in azimuth by stepping through subarrays, one at a time, and beamforming so as to produce scanlines normal to the face of the subarray. With this design, fewer elements are required along the elevation dimension because it is kept deliberately small, to produce an elongated sector volume. In azimuth, fewer elements are needed because the elements are spaced further apart (as much as $2\lambda$) since phased-array scanning is not used in this dimension. In other words, the 2D array is sparse in the azimuth dimension. The transducer elements used are square in shape and less than or equal to $0.75\lambda$ in size.

OBJECTS OF THE INVENTION

An object of the present invention is to provide ultrasound imaging technology which may be incorporated in practical, affordable, high-quality, 3D ultrasound imaging systems which are clinically useful, and which exploit 3D, electronic, volume data acquisition.

Another object of the present invention is to provide 3D ultrasound systems using state-of-the-art elemental transducer technology (e.g. using 1.75D transducer technology), switching, multiplexer and cable technology, and real-time signal processing technology such as ASIC beamforming and filtering hardware.

The most significant cost and complexity in premium 2D ultrasound systems relates to the receive electronics, the cost of which is proportional to the number of digital receive channels. For affordability therefore, another object of the present invention is to keep the number of digital receive channels in the contemplated 3D ultrasound systems similar to that provided in current premium 2D ultrasounds.

A further object of the present invention is that the 2D probe apparatus and beamforming methods disclosed provide high-quality volume data which can be used to generate high-quality 3D imagery (e.g. 3D surface rendering or orthographic presentations) as well as 2D imagery of similar or better quality than premium, state-of-the-art, 2D ultrasound systems currently produce. High-quality imagery is characterized by azimuth, elevation and range resolutions equal to or better than that provided by premium 2D ultrasound systems, as well as grating lobe beam responses (or sidelobe responses for narrowband systems) similar to that provided by premium 2D systems.

It is another object of the present invention to provide azimuth resolution that is significantly better than that of a premium 2D ultrasound system using the same azimuth aperture.

It is another object of the present invention to provide means to produce elevation resolution significantly better than that provided by premium 1.5D arrays in use today.

It is another object of the present invention to provide fully-electronic, 3D volume data acquisition to support rapid and accurate interrogation of volumes combined with highest-quality, 3D image formation.

In order to maximize the clinical utility of the 3D ultrasound system contemplated with the present invention, it is an object of the invention to minimize the 3D volume acquisition time to sustain the highest 3D frame rates without significantly sacrificing affordability or image quality. For example, it is an object of the present invention is that meaningful, high-quality 3D data cubes can be electronically acquired in a fraction of one second.

Another object of the present invention is to provide 2D probe and beamforming technology that can be manufactured in a conformal form factor, and be used as a building block (i.e. providing transmission apertures and data gathering apertures) in ultrasound medical imaging systems, exemplarily as described in U.S. Pat. Nos. 5,666,953, 5,871,446, 6,023,632, 6,319,201, and 6,106,463

Another object of the present invention is to provide a compact and deployable 3D ultrasound system of size, weight, power, and form-factor similar to conventional 2D ultrasound systems.

Yet another object of the present invention is to increase the image quality of light-weight, portable, 2D ultrasound imaging systems employing fewer receive channels than premium 2D ultrasounds, without appreciably increasing the size or cost of such improved systems.

Another object of the present invention is to provide an ultrasound system for 3D imaging of the carotid artery, providing improvements in safety and accuracy over current diagnostic methods.

A further object of the present invention is to provide ultrasound technology permitting a standard 2D ultrasound medical procedure to be carried out more quickly and hence more safely.

An additional object of the present invention is to provide ultrasound technology enabling a relatively unskilled medical practitioner the ability to perform an ultrasound medical procedure.

Further objects of the invention will be apparent from the drawings and descriptions herein. It is to be noted that each object is achieved by at least one embodiment of the present invention. However, it is not necessary that any given embodiment achieve all of the objects of the invention.

SUMMARY OF THE INVENTION

The present invention addresses the above-mentioned difficulties by employing innovative approaches which together provide a practical solution to ultrasound imaging systems employing 2D ultrasonic arrays which support electronic, 3D volume data acquisition and beamforming.

The present invention is directed in part to a probe for electronic, 3D volume data acquisition using ultrasound, comprising a plurality of transducer elements arranged in a two dimensional array having an azimuth dimension and an elevation dimension. The transducer elements have a first element size in the azimuth dimension and a second element size in the elevation dimension. In a preferred embodiment, at least one of the first and second element sizes is at least twice a characteristic wavelength of a waveform used to drive the array of transducer elements, where the characteristic wavelength is defined as the wavelength corresponding to a center frequency of the waveform.

In a particular embodiment, an ultrasound imaging transducer in a system in accordance with the present invention exploits 1.75D elemental technology (Puyun Guo, Shikui Yan and Quing Zhu, "Elevation Beamforming Performance of a 1.75D array", IEEE 2001 Ultrasound, Ferroelectronics and Frequency Control Conference).

An ultrasound imaging transducer in a system in accordance with the present invention can be manufactured in a conformal form factor, and be used as a building block (i.e., a 2D transducer array module) in ultrasound blanket systems as disclosed in U.S. Pat. No. 5,666,953 and its progeny.

The present invention is also directed to a method of generating image data in a scanning process, using a CAC-BF (see below) technique in at least one of an azimuth dimension and an elevation dimension, to form an ultrasound image line, image plane, or image data cube. The CAC-BF method can be applied advantageously to any 1D or 2D ultrasonic probe or array, and is not restricted to the preferred embodiments disclosed herein.

The present invention includes a novel beamforming method (CAC-BF) that produces high-resolution ultrasound images more efficiently than conventional methods. CAC-BF divides the transducer into a number of smaller subapertures, each of which transmits and receives a number of low-resolution beams that span the imaged region. High resolution is obtained at each image point by coherently combining the beamformed signals from the subapertures, synthesizing a large aperture focussed at the point.

The present invention provides practical, clinically useful, high-resolution, 3D ultrasound, electronic, volume data acquisition.

An ultrasound imaging system in accordance with the present invention exhibits 3D imaging with voxel resolution equal to or better than that of state-of-the-art planar images, in both the azimuth and elevation dimensions. In one preferred embodiment, the voxel resolution is twice as good in azimuth and/or elevation as that in state-of-the-art planar images.

An ultrasound imaging system in accordance with the present invention is relatively inexpensive to manufacture. The imaging system can be implemented as an inexpensive upgrade to existing premium ultrasound systems, or as a stand-alone solution of comparable cost to state-of-the-art 2D ultrasound systems.

In a particular embodiment, an ultrasound system in accordance with the present invention is able to electronically acquire the 3D data cube of size 26 mm×26 mm by 70 mm spanned by the transducer in under one second.

As with any new imaging technology, it's usefulness must be proven clinically using one or more clinical applications. The initial target application of the present invention is the carotid artery, although there is nothing that would restrict its use in other applications (e.g. obstetrics and gynecology). This clinical application involves diagnosing plaque in the carotid artery, which can be fatal if left untreated. Presently, high frequency (7.5 MHz), wideband linear arrays (that use sequenced azimuth scanning) are used primarily for ultrasound imaging of the carotid artery. State-of-the-art, 1.5D probes produce rectangular images that span about 3 cm (in azimuth) by 7 cm (in depth), and whose image quality is characterized by an F number of 2 in azimuth and 8 in elevation. The ability to electronically acquire a data cube (rather than just a plane) and to improve the elevation resolution to an F number of 4 are highly desirable for this application. The present invention delivers such improvements affordably.

It is obvious to one skilled in the art that there is more to building a 2D or 3D ultrasound imaging system as contemplated herein than simply employing the disclosed 2D arrays or CAC-BF method. The design and implementation of a complete probe, beamformer or ultrasound imaging system assumes a large amount of hardware, software, and systems engineering and manufacturing knowledge known to those skilled in the art. For example, the 2D probe array technology disclosed herein requires array manufacturing, power, switching electronics, cabling, and housing considerations to be determined for a particular implementation. When the CAC-BF method is applied to a 1D probe array or 2D probe array as disclosed herein, special switching and/or cabling considerations known to those skilled in the art are needed. For each desired beam, contiguous sets of elements associated with the subapertures used by the CAC-BF method must be switched or electrically connected to the cabling which feeds the received signals to the receive electronics and beamformers. Particular probe embodiments, all within the scope of the present invention, are realized by employing combinations of switching and multiplexing electronics known to those skilled in the art, to trade-off cost, performance and complexity of the resulting probe. Switching and multiplexing electronics may be contained entirely within the probe housing, or distributed between the probe housing and the ultrasound engine containing the receive electronics, without departing from the spirit and scope of the present invention. While it is a preferred embodiment of the present invention for the CAC-BF coarse and fine beamforming operations to be performed digitally in the ultrasound engine, this functionality can also be distributed throughout the entire ultrasound system, and be implemented in hardware or software in a variety of ways known to those skilled in the art, without departing from the scope of the present invention. In addition, post-beamforming operations such as vector processing and imaging processing are also known to those skilled in the art, and any conventional form of these operations could obviously be used effectively with the disclosed inventions.

Comparison of Invention with Prior Art

While U.S. Pat. No. 6,106,471 "Procedure for an Examination of Objects by the Means of Ultrasound Waves" describes a practical solution to 3D ultrasound imaging, it is fundamentally different from the present invention. The present invention uses electronic scanning in both the azimuth and elevation dimensions, affording higher 3D image quality over the mechanical, elevation scanning solution provided in U.S. Pat. No. 6,106,471.

The probe or imaging transducer of the present invention is similar to the 2D array disclosed in U.S. Pat. No. 6,238,346 in that 3D volume acquisition is done electronically, and both attempt to reduce the number of transducer elements without degrading sidelobe performance. However, there are several significant differences. The 2D array in U.S. Pat. No. 6,238,346 uses square elements which are spaced sparsely in the azimuth dimension which reduces sensitivity and increases grating lobes. The present invention does not use a sparse arrangement of elements. Rather, it uses rectangular elements whose size in azimuth results in a similar reduction in number of elements, without reducing sensitivity. The imaging transducer of the present invention has switching circuitry to form subarrays of transducer elements, each consisting of a contiguous subset of azimuth elements and a contiguous subset of elevation elements. Adjacent subarrays in the azimuth dimension typically require an overlap of about 50% of the number of azimuth elements in the subarray for optimal performance. The 2D array in U.S. Pat. No. 6,238,346, on the other hand, forms subarrays by switching in subsets of contiguous elements in the azimuth dimension, but using all of the elements in the elevation dimension. Furthermore, adjacent subarrays in azimuth are only shifted by a single element (i.e. they require a much greater overlap than 50%). The imaging transducer array of the present invention preserves the state-of-the-art, B-mode planar image; whereas the 2D array in U.S. Pat. No. 6,238,346 does not.

The present invention, like that described in U.S. Pat. No. 6,419,633 "2D Ultrasonic Transducer Array for Two Dimensional and Three Dimensional Imaging" is concerned with a 2D electronic transducer array which can be configured to support both 2D imaging and 3D imaging. However, the present invention performs differently in three key ways as a result of its CAC-BF method and its preferred transducer design. First, it not only preserves 2D planar image quality (as compared to that afforded by optimized 1D arrays), it provides an azimuth resolution that is significantly better. Second, it does not use a 2D sparse array for 3D imaging; rather, it uses a full array; hence, the present invention does not suffer reduced sensitivity, and grating lobes are avoided by using sequential scanning in elevation when larger elements (greater than $\lambda$) are used. Finally, while the invention disclosed in U.S. Pat. No. 6,419,633 does reduce the number of signal leads (and hence channels) otherwise required, the reduction is not sufficient for the objectives of the present invention. For example, an instantaneous aperture to achieve F/2 in azimuth and F/4 in elevation with a conventional element size $\lambda$ requires a fully populated array of at least 128-by-64 elements. Using the sparse 2D configuration of U.S. Pat. No. 6,419,633 still requires $64 \times 32 = 2{,}048$ signal leads and channels, which is an order of magnitude larger than that needed by the present invention. As a result, the present invention is better suited to premium image quality applications requiring larger apertures.

In U.S. Pat. No. 6,482,160 "High Resolution 3D Ultrasound Imaging System Deploying a Multidimensional Array of Sensors and Method for Multidimensional Beamforming Sensor Signals", Stergiopoulos and Dhanantwari describe a method for processing the signals received from a 2D electronic, ultrasonic array. Both the assumed transducer array, and the processing method employed are fundamentally different from the present invention. The assumed transmit sensor is a single, low-gain transducer element which illuminates the entire region being imaged, causing ultrasound energy to reflect back towards a receiving array. The region being imaged is assumed to be in the far-field of the receive array, and a conventional, 2D electronic scanning receive array is assumed. In the case of the present invention, the transmit aperture is a high-gain aperture (made up of several receive elements), and for the case of the preferred CAC-BF method disclosed herein, the same aperture is used for each transmit/receive scan-line pair. The region being imaged can be in the near-field of the receiving array of the present invention (which is the case for the carotid artery application disclosed herein). The array element feature sizes are not conventional for the disclosed, preferred 2D array transducer. The beamforming method used in U.S. Pat. No. 6,482,160 is very different that the CAC-BF method of the present invention. First, the CAC-BF method works very well when the object being imaged is in the near-field of the receiving array, but the method of U.S. Pat. No. 6,482,160 only applies to far-field imaging. It employs adaptive beamforming algorithms to increase spatial resolution over that obtainable from conventional beamformers; however, the inventors acknowledge that their beamformer's performance can degrade significantly if the assumed noise characteristics are inaccurate. The CAC-BF method of the present invention also increases spatial resolution; however, it makes no assumptions about the noise characteristics and hence is more robust.

DETAILED DESCRIPTION OF THE PREFERRED EMBODIMENTS

Figure 1A:
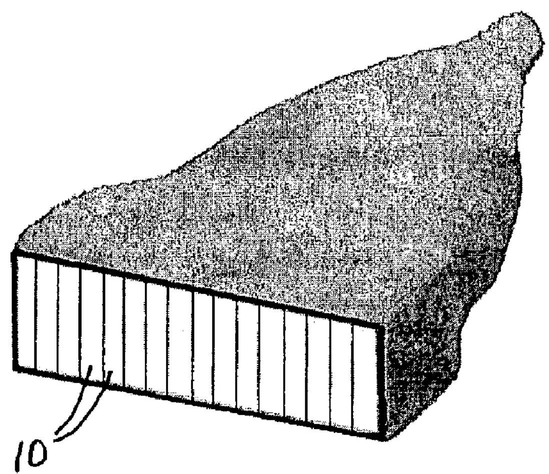
FIG. 1A is a schematic perspective view of a prior-art 1D linear array of ultrasonic scanning sensing elements.
Figure 1B:
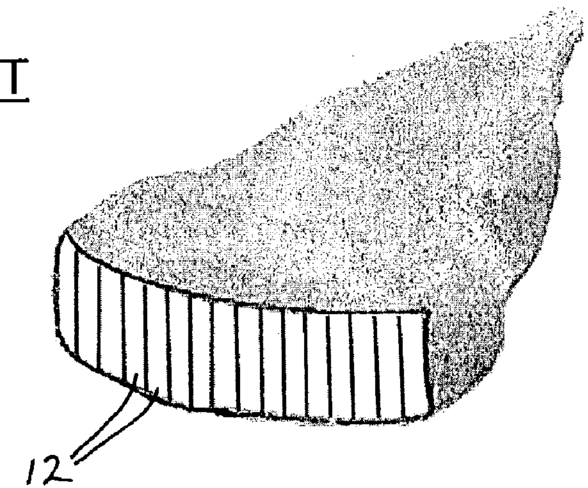
FIG. 1B is a schematic perspective view of a prior-art 1D curved array of ultrasonic scanning sensing elements.
Figure 2A:
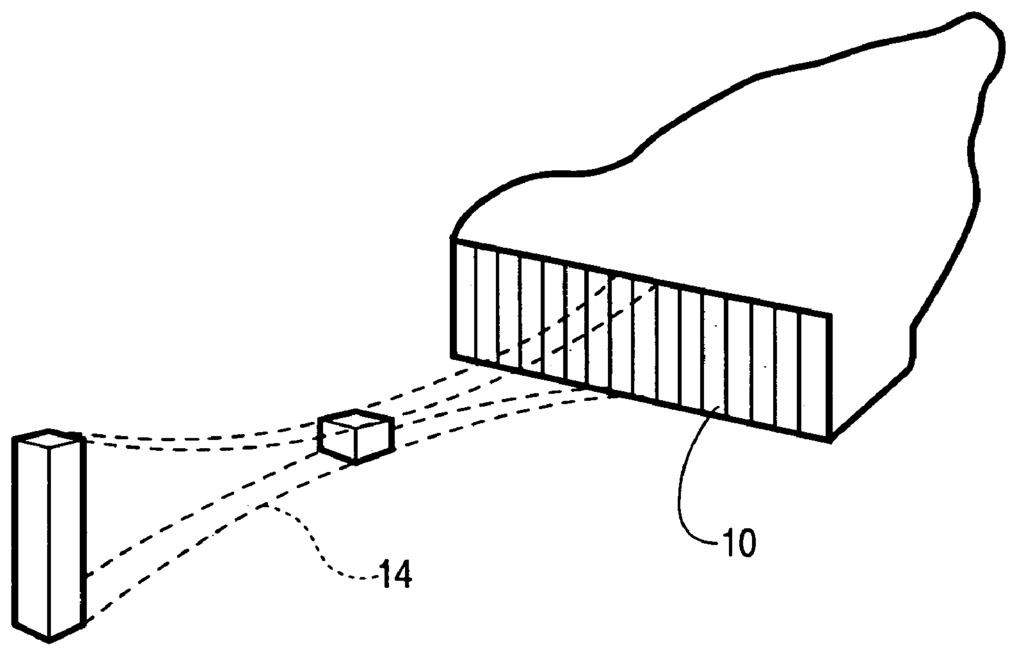
FIG. 2A is a schematic perspective view of the beam produced by a prior-art 1D linear array of ultrasonic scanning or sensing elements.
Figure 2B:
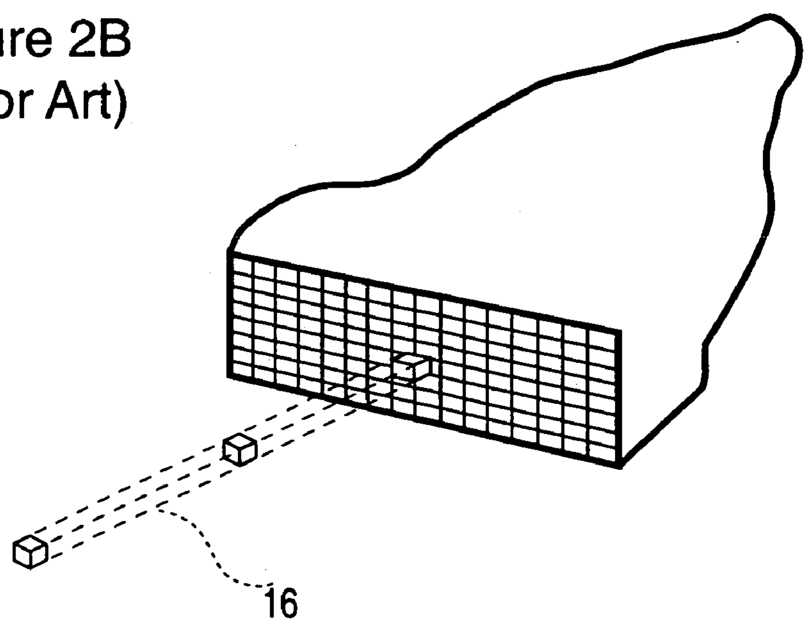
FIG. 2B is a schematic perspective view of the beam produced by a prior-art 1.5D linear array of ultrasonic scanning or sensing elements
Figure 3A:
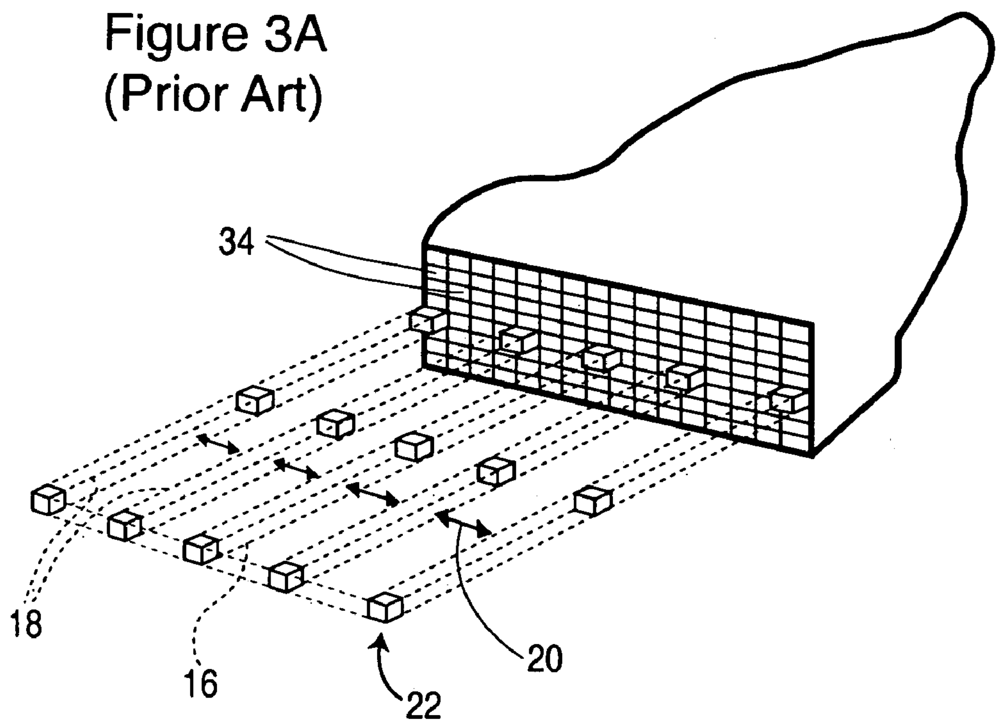
FIG. 3A is a schematic perspective view of a prior-art 1.5D linear array of ultrasonic scanning or sensing elements with sequential scanning in azimuth.
Figure 3B:
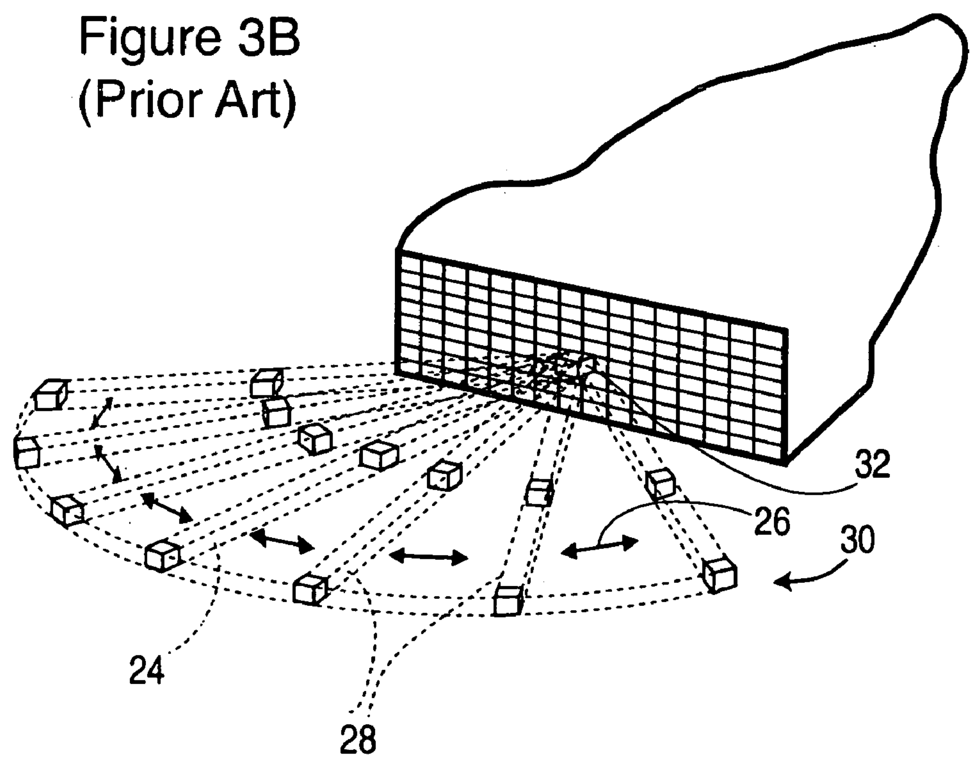
FIG. 3B is a schematic perspective view of a prior-art 1.5D linear array with phased-array scanning in azimuth.
Figure 4:
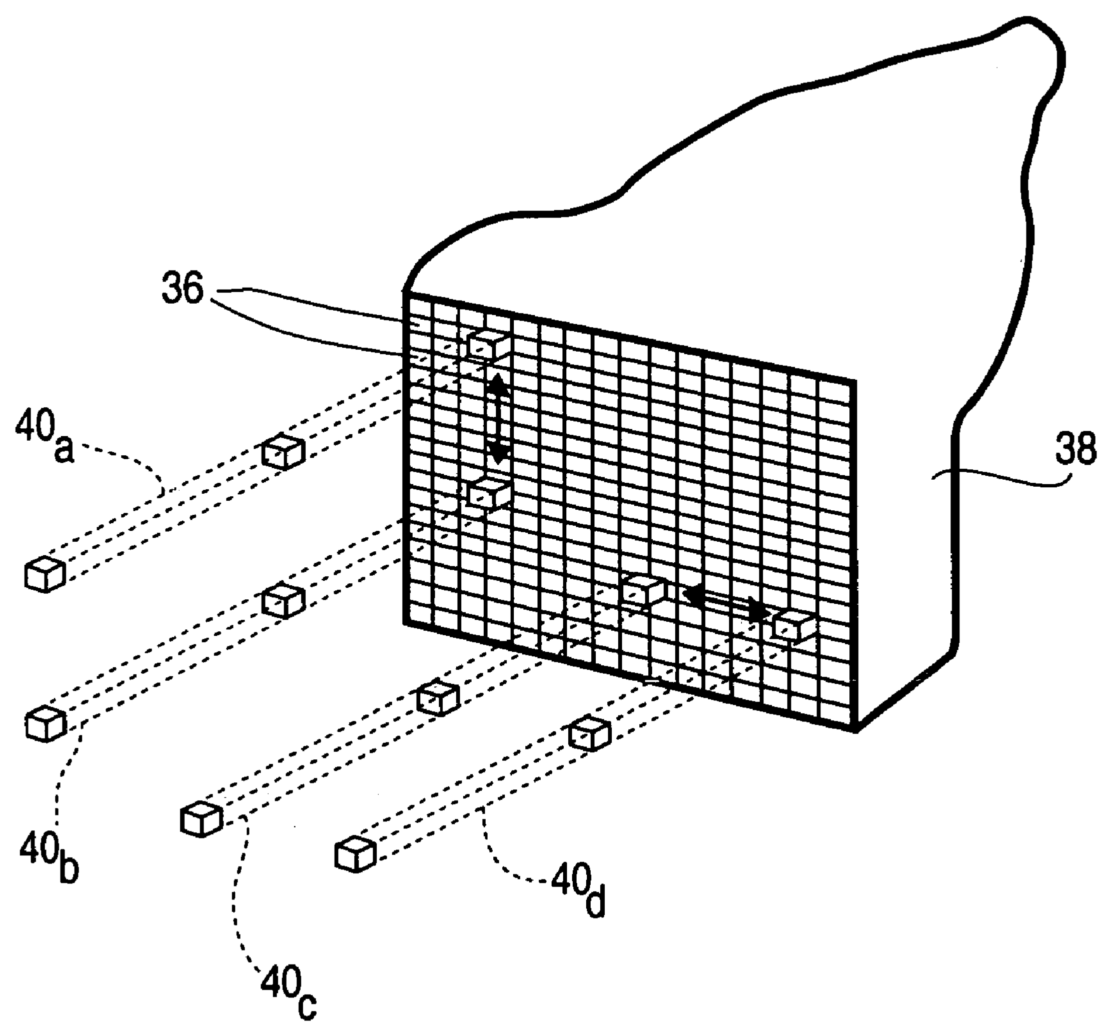
FIG. 4 is a schematic perspective view of a 2D ultrasonic transducer array pursuant to the present invention.

FIG. 4 shows an ultrasound transducer probe where scanning occurs in both the azimuth dimension (i.e., horizontally) and in the elevation dimension (vertically). The probe includes a rectangular array of transducer elements 36 mounted to a holder or substrate member 38. Four different beams 40*a*, 40*b*, 40*c*, 40*d* are illustrated in FIG. 4, demonstrating that the probe is capable of illuminating a volume. The transducer elements 36 can be controlled to effect sequential scanning in azimuth and elevation as illustrated in FIG. 4; but nothing prevents one from using phased-array scanning or CAC-BF (coherent aperture combining beamforming) scanning (see below) in azimuth and/or elevation. If phased array scanning is used in a given dimension, the acquired data usually is scan converted (i.e. transformed or mapped onto a Cartesion grid) in order to present the image on a conventional display (i.e. a monitor using a cathode ray tube (CRT)). The net effect of any of these scanning techniques is that a volume of ultrasound data is ultimately acquired electronically, which ultimately can be represented on a Cartesian (x-y-z) grid.

A preferred embodiment of the ultrasound transducer device or probe of FIG. 4 for 3D imaging of the carotid artery is characterized by the following baseline parameters:

256×40 piezoelectric transducer elements 36

0.2 mm (λ)×0.8 mm (4λ) element spacing in azimuth and elevation, respectively

Scans in azimuth and elevation

Uses 128-elements for azimuth instantaneous aperture

Uses 20% elevation instantaneous aperture (i.e. 8-element subaperture)

TX focal depth is 50 mm

Imaging depth is typically 0 to 7 cm

Nominal azimuth resolution of F/2

Nominal elevation resolution (using 8 elevation elements per beam) of F/8

High elevation resolution (using 16 elevation elements per beam) of F/4

Frequency 7.5 MHz (central wavelength 0.2 mm)

Pulse length 0.4 mm (0.27 μs) with Hann weighting, yielding approximately 100% bandwidth 128 digital receive channels image volume 25.6 mm×25.6 mm×70 mm It should be noted that any of the above parameters, including the frequency, can be changed for other applications in order to create other preferred embodiments, and such changes would not depart from the spirit or scope of the probe in accordance with the present invention.

An ultrasound transducer device or probe, as shown in FIG. 4, characterized by these parameters produces an image data cube of dimension 25.6 mm (elevation) by 25.6 mm (azimuth) by 70 mm (depth). (The dimension of the data cube can change without changing the basic design of the 2D ultrasound transducer device or carotid-scanning probe.) The 2D ultrasound transducer device or carotid-scanning probe operates at 7.5 MHz so the wavelength, λ, is nominally 0.2 mm. The ultrasonic carotid artery scanner therefore uses elements that are nominally spaced (and sized, neglecting kurfs) 4λ (elevation) by λ (azimuth). A key feature of the ultrasound transducer device or carotid-scanning probe is the large elemental size in elevation. Sequential scanning is assumed to scan in the elevation dimension. The λ spacing in azimuth supports both sequential scanning, as well as phased-array type scanning. Phased array scanning is usually limited to about ±45 deg to avoid grating lobes.

Consider the case of sequential scanning in azimuth, where 128 elements are used at any one time so the instantaneous azimuth aperture is 128×0.2 mm=25.6 mm. At 50 mm depth, this leads to an F/2 which is desired. Since it is desired that the image extent in azimuth is also 25.6 mm, 256 elements are needed in total, where 128 of them are used for any given vector. In elevation, the total array spans 40*0.8 mm=32.0 mm. However, a sub-aperture of 8 elements (consistent with state-of-the-art 1.5D arrays) spans 6.4 mm. Elevation vectors that are not degraded due to asymmetries must not be closer than 3.2 mm (6.4/2) from the edge of the ultrasound transducer device or carotid-scanning probe. Therefore the useable elevation dimension is 32.0 mm−2*3.2=25.6 mm.

The azimuth dimension of stated volume can be larger than 25.6 mm because on transmit, one generally only uses an F/5 (i.e. about 50 elements), instead of the 128 elements used on receive. One should also note that if phased-array scanning is used in azimuth, then only 128 elements are needed in azimuth (rather than 256 as for sequential scanning).

The aforementioned 2D transducer device of FIG. 4 has several advantages over the conventional 2D array described earlier. The conventional 2D array requires at least four times the number of elements to scan the same volume (assuming the azimuth and elevation element sizes are both λ). If a conventional probe restricts itself to the same number of elements as the 2D transducer device disclosed herein, then it will also result in lower spatial resolution and image quality because the physical aperture will be smaller. As a result, the 2D transducer device in accordance with the present invention is more practical, less complex and less expensive than a similarly performing conventional 2D array.

For practicality and affordability, the preferred embodiment of the present invention uses only say 128 receive channels, consistent with that found in premium 2D ultrasound systems. To form beams with state-of-the-art resolutions of F/2 in azimuth and F/8 in elevation using the probe of FIG. 4, then 128×8=1024 elements are needed in the formation of each beam. If a higher elevation resolution is desired, say F/4, then 16 elevation elements are needed and hence 2,048 elements to form each beam. This poses a problem, since one is restricted to only 128 receive channels. Conventionally, synthetic aperture methods would be used to acquire the received signals, 128 elements at a time, using at least 8 and 16 shots, respectively, for the F/8 and F/4 beams. The number of shots would be even larger if a synthetic aperture mode is also required on transmission. The problem with using the synthetic aperture approach for the 2D probe of FIG. 4 is that the acquisition or frame time associated with acquiring the desired 3D volume increases proportionately to the number of shots required. As it is an object of the present invention to also reduce the acquisition or frame time, the CAC-BF method has been developed for this purpose. This method results in significant reductions in acquisition time, while not degrading image quality.

CAC-BF scanning, discussed in detail below, forms part of the present invention. It is used with the probe of FIG. 4, or any other 1D or 2D probe, when it is necessary to minimize the volumetric or image acquisition time. The baseline CAC-BF configuration is a preferred embodiment of the CAC-BF method which uses sequential scanning in elevation, combined with CAC-BF in azimuth. For F/2 in azimuth and F/8 in elevation, the CAC-BF subapertures are typically of dimension $16_{az}\times8_{el}$ (i.e. each subaperture has 16 contiguous elements in azimuth and 8 in elevation for a total of 128), and twenty (20) subapertures are used in total to span the 128 element azimuth aperture desired, where adjacent, azimuth subapertures have an overlap of 10 azimuth elements. Typically 10 phased-array type beams are formed for each subaperture, and the collection of resulting beams from all apertures are coherently combined to produce the final image. If higher F/4 elevation resolution is desired, then a total of forty-one (41) $8_{az}\times16_{el}$ subapertures are typically used, with adjacent subapertures having an overlap of 5 elements in azimuth. For a given application, the size and number of the subapertures, their overlap, and the number and spacing of beams formed per subaperture are optimized to yield the required performance.

Coherent Aperture Combining Beamforming: In General

In a preferred embodiment, the 2D ultrasound transducer device or carotid-scanning probe of FIG. 4 uses a novel beamforming technique referred to as coherent aperture combining beamforming (CAC-BF) to achieve substantially reduced volume acquisition times while maintaining imaging performance.

The general concept underlying CAC-BF will now be described with reference to FIG. 5A. A volume 42 to be imaged is divided into a Cartesian grid of points (voxels), nominally separated by the achievable resolution in each dimension. A number of subapertures $\mathbf{44}_a$, $\mathbf{44}_b$, . . . $\mathbf{44}_n$ are defined within the ultrasound transducer device or carotid-scanning probe. A number of beams $\mathbf{46}_{a1}$, $\mathbf{46}_{a2}$, . . . $\mathbf{46}_{ai}$, $\mathbf{46}_{b1}$, $\mathbf{46}_{b2}$, . . . $46b_j$, . . . $\mathbf{46}_{n1}$, $\mathbf{46}_{n2}$, . . . $\mathbf{46}_{nk}$ from each subaperture $\mathbf{44}_a$, $\mathbf{44}_b$, . . . $\mathbf{44}_n$ are directed towards different angles collectively spanning the volume of interest 42. High-resolution voxels are formed by summing signals from a number of low-resolution (coarse) beams originating from different subapertures $\mathbf{44}_a$, $\mathbf{44}_b$, . . . $\mathbf{44}_n$. High resolution is achieved because the summation results in the full aperture (i.e. the total extent of the subapertures) being synthesised and focussed at each voxel in the image. The low-resolution ultrasound beamformed signals $\mathbf{46}_{a1}$, $\mathbf{46}_{a2}$, . . . $\mathbf{46}_{ai}$, $\mathbf{46}_{b1}$, $\mathbf{46}_{b2}$, . . . $46b_i$, . . . $\mathbf{46}_{n1}$, . . . $\mathbf{46}_{nk}$ from subapertures $\mathbf{44}_a$, $\mathbf{44}_b$, . . . $\mathbf{44}_n$ each have a relatively large beam width, that is, a relatively low or coarse spatial resolution, the spatial resolution of each of the beamformed signals $\mathbf{46}_{a1}$, $\mathbf{46}_{a2}$, . . . $\mathbf{46}_{ai}$, $\mathbf{46}_{b1}$, $\mathbf{46}_{b2}$, . . . $\mathbf{46}_i$, . . . $\mathbf{46}_{n1}$, $\mathbf{46}_{n2}$, . . . $\mathbf{46}_{nk}$ being less than the spatial resolution of the image data in the final image, which corresponds to the composite aperture formed by the summation process. The resolution is thus inversely related to the length dimension or size of the respective subaperture $\mathbf{44}_a$, $\mathbf{44}_b$, . . . $\mathbf{44}_n$ or composite aperture. The subapertures $\mathbf{44}_a$, $\mathbf{44}_b$, . . . $\mathbf{44}_n$ have a small linear dimension or size and a coarse or large-grained ("low") resolution, while the composite aperture has a large linear dimension or size and a fine or small-grained (high) resolution. The coherently combining of received low-resolution beamformed signals $\mathbf{46}_{a1}$, $\mathbf{46}_{a2}$, . . . $\mathbf{46}_{ai}$, $\mathbf{46}_{b1}$, $\mathbf{46}_{b2}$, . . . $\mathbf{46}_{bj}$, . . . $\mathbf{46}_{n1}$, $\mathbf{46}_{n2}$, . . . $\mathbf{46}_{nk}$ from subapertures $\mathbf{44}_a$, $\mathbf{44}_b$, . . . $\mathbf{44}_n$ synthesizes a composite aperture having a larger length dimension or size than any one of the subapertures and focused at each point of the scanned volume. resulting in image data at each point of that volume having a spatial resolution higher than the spatial resolution of any one of the beamformed signals $\mathbf{46}_{a1}$, $\mathbf{46}_{a2}$, . . . $\mathbf{46}_{ai}$, $\mathbf{46}_{b1}$, . . . $46b_j$, . . . $\mathbf{46}_{n1}$, $\mathbf{46}_{n2}$, . . . $\mathbf{46}_{nk}$ in accordance with the larger length dimension or size of the composite aperture.

The differences between a method and apparatus using conventional techniques and a method and apparatus utilizing CAC-BF are as follows. Conventional techniques are organized into two categories: those using synthetic aperture beam formation, and those not. We consider the latter first. In a conventional ultrasound (without synthetic aperture beam formation), beams are fully formed, both on transmit and receive, with a single shot. The number of elements in the aperture is thus limited by how many channels are available. The transmit aperture is restricted to be smaller than the receive subaperture to provide a reasonable depth of focus. This means that with the receive hardware currently available (i.e. we do not want to increase the number of receive channels in premium 2D ultrasound systems), high-resolution 2D electronic scanning is not practical. The CAC-BF method differs from high-resolution conventional beamforming in two key ways. First, conventional beamformers do not use subapertures $\mathbf{44}_a$, $\mathbf{44}_b$, . . . $\mathbf{44}_n$ in the beamforming process. Second, conventional beamformers transmit on a smaller aperture than they receive on.

In conventional systems with 'synthetic aperture' beamforming, a number of subapertures (offset in azimuth only) are focussed along a given range line on consecutive shots, and then the return signals are summed in order to synthesize a single beam. If a high-resolution transmit beam is also needed, then multiple subapertures are used on transmit for each receive subaperture; shots that have different transmit and receive subapertures are 'cross-terms' in the summation. Interestingly, cross-terms actually decrease resolution, but do help to reduce sidelobes. Current premium ultrasounds, when operating in synthetic aperture mode, typically use only two subapertures on receive (There is usually one direct transmitlreceive and one cross-term transmit/receive. For example, transmit on a central subaperture and receive on central subaperture, followed by transmit on central and receive on outer subaperture.). Several key differences exist between the CAC-BF method and synthetic aperture beamforming. First, there are no cross-terms in the baseline CAC-BF concept as used herein, that is, each of the beamformed signals 46$_{a1}$, 46$_{a2}$, . . . 46$_{ai}$, 46$_{b1}$, 46$_{b2}$, . . . 46b$_j$, . . . 46$_{n1}$, 46$_{n2}$, . . . 46$_{nk}$ is formed by selectively energizing and selectively polling only transducers in a single respective one of the subapertures 44$_a$, 44$_b$, . . . 44$_n$ (for each of said beamformed signals, a respective one of said subapertures is used for both transmitting and receiving). The result is that resolution is better for CAC-BF. Second, whereas synthetic aperture beamformers form a single high-resolution beam for each voxel, the CAC-BF method forms several coarse, low-resolution beams and combines them at each voxel. Third, in a preferred embodiment of CAC-BF, each low-resolution beam is formed using transmit and receive subapertures that are the same size. In synthetic aperture beamforming, the transmit and receive subapertures used for beam formation are different in size, the transmit being smaller.

In a given region, the CAC-BF concept contemplates that each low-resolution beam is transmitted and received from the same (sub)aperture. High-resolution 'beams' are not really formed; rather a high-resolution aperture is synthesized at each voxel. Multiple low-resolution beams from each subaperture cover a region spanning many beamwidths. The ultrasound imaging process utilizing CAC-BF breaks up the existing large aperture.

A conventional ultrasound may also transmit multiple shots to get better depth of field (one shot for each range interval). This is because the transmit beam must be focussed at a particular range, and only voxels for ranges within its depth of focus can use the beam. To cover a wide range swath, a sequence of shots are transmitted along each range line, each focussed at a different range. This forces the system to take more time to cover the volume. The higher the resolution, the smaller is the depth of focus, and hence the longer it takes to image a volume. With the disclosed CAC-BF method, the depth of focus is defined by the resolution of the coarse beams, giving it a natural advantage over state-of-the-art beamforming methods. This is a fundamental difference between conventional beamforming methods and the CAC-BF method. The preferred embodiments of the CAC-BF described herein only require a single shot per range line or image vector.

Figure 5B:
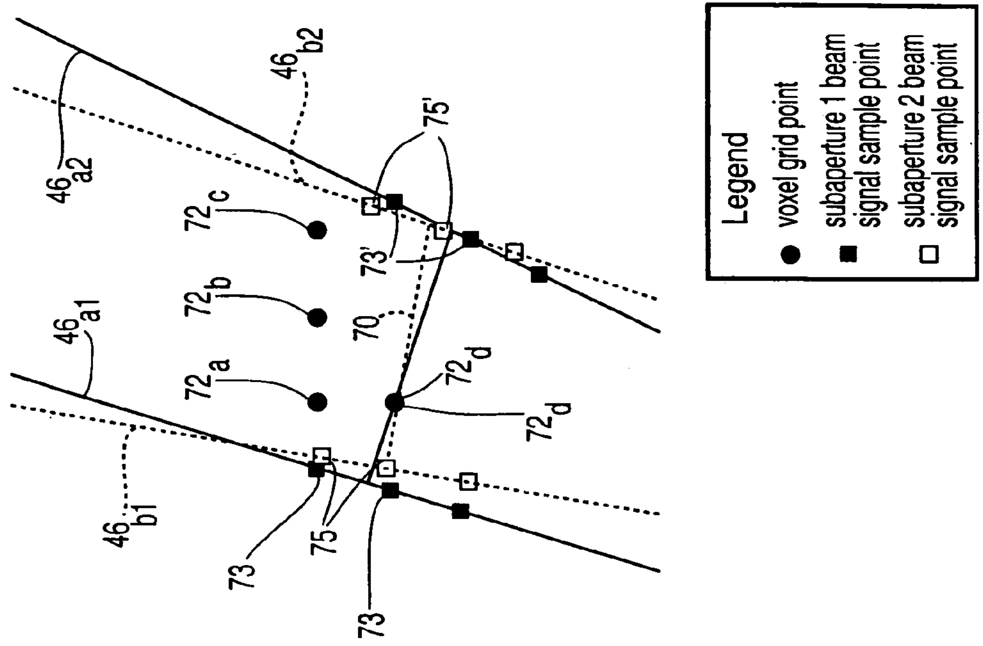
FIGS. 5A and 5B are a diagram illustrating basic CAC-BF concepts utilized in carrying out the present invention.
Figure 5A:
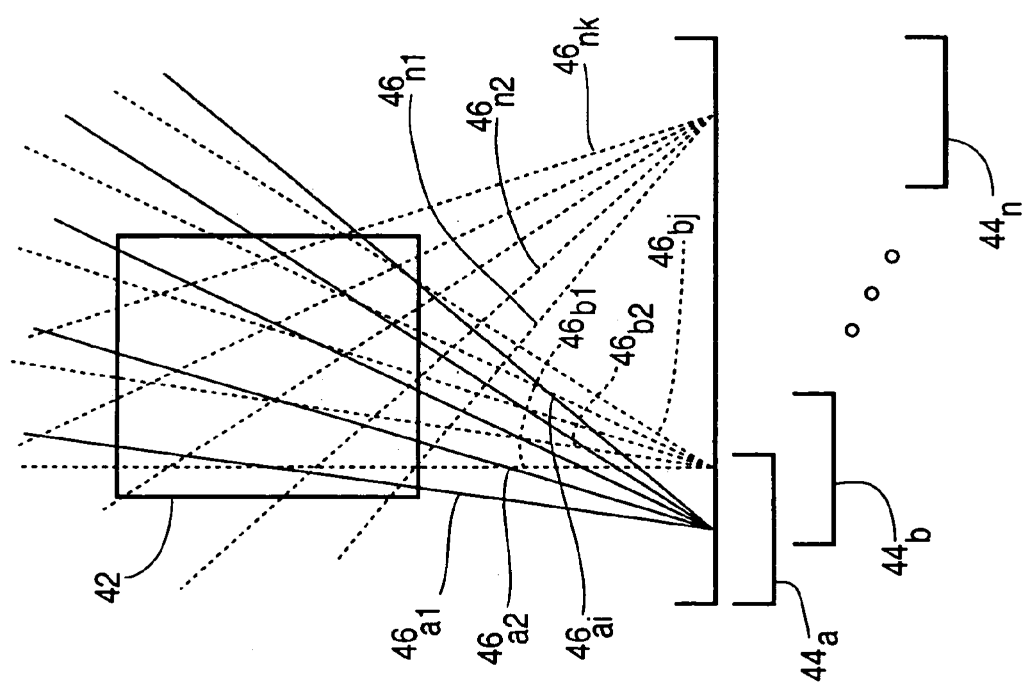

The ultrasound transducer device or carotid-scanning probe (see FIG. 4) is divided or partitioned into overlapping subapertures 44$_a$, 44$_b$, . . . 44$_n$ (FIG. 5A). These are composed of (say) 64 to 128 elements to match the available number of signal receive channels. In a preferred embodiment, the subapertures 44$_a$, 44$_b$, . . . 44$_n$ overlap by at least 50% of their width in each dimension (azimuth or elevation) where CAC-BF is applied. The percentage overlap strongly affects the impulse response of the resulting, high-resolution, CAC-BF image. Grating lobes may result if enough overlap is not selected. FIG. 5 shows a 1D array partitioned along the azimuth dimension into subapertures 44$_a$, 44$_b$, . . . 44$_n$. CAC-BF is illustrated below for this single azimuth dimension. Extension of CAC-BF applied to two dimensions (i.e. azimuth and elevation) is straightforward.

Coherent Aperture Combining Beamforming: Image Partition

The image space 42 is divided into overlapping beams 46$_{a1}$, 46$_{a2}$, . . . 46$_{ai}$, 46$_{b1}$, 46$_{b2}$, . . . 46$_{bj}$, . . . 46$_{n1}$, 46$_{n2}$, . . . 46$_{nk}$ from each subaperture 44$_a$, 44$_b$, . . . 44$_n$. FIG. 5A shows the beam boresights as lines originating from the subapertures 44$_a$, 44$_b$, . . . 44$_n$, and travelling through the volume 42. Each subaperture 44$_a$, 44$_b$, . . . 44$_n$ transmits and receives a respective sequence of overlapping (coarse) phased-array beams 46$_{a1}$, 46$_{a2}$, . . . 46$_{ai}$, 46$_{b1}$, 46$_{b2}$, . . . 46b$_j$, . . . 46$_{n1}$, 46$_{n2}$, . . . 46$_{nk}$, each beam being focussed at a different angle. A pulse (shot) is transmitted and a range line is received for each beam 46$_{a1}$, 46$_{a2}$, . . . 46$_{ai}$, 46$_{b1}$, 46$_{b2}$, . . . 46b$_j$, . . . 46$_{n1}$, 46$_{n2}$, . . . 46$_{nk}$ from each subaperture 44$_a$, 44$_b$, . . . 44$_n$. The beams for each subaperture are normally spaced so that they cross at approximately their −3 dB points. To avoid grating lobes, the total angle (volume) spanned by the beams 46$_{a1}$, 46$_{a2}$, . . . 46$_{ai}$, 46$_{b1}$, 46$_{b2}$, . . . 46b$_j$, . . . 46$_{n1}$, 46$_{n2}$, . . . 46$_{nk}$ from each subaperture 44$_a$, 44$_b$, . . . 44$_n$ is usually limited by the reciprocal of the element spacing weighted by a constant that takes into account unit conversion. This consequently limits the size of the full aperture that can be synthesized. Only beams that intersect the imaged volume 42 need be transmitted, thereby saving additional acquisition time; thus subapertures at the edges of the volume transmit fewer beams.

Coherent Aperture Combining Beamforming: Image Formation

Figure 6:
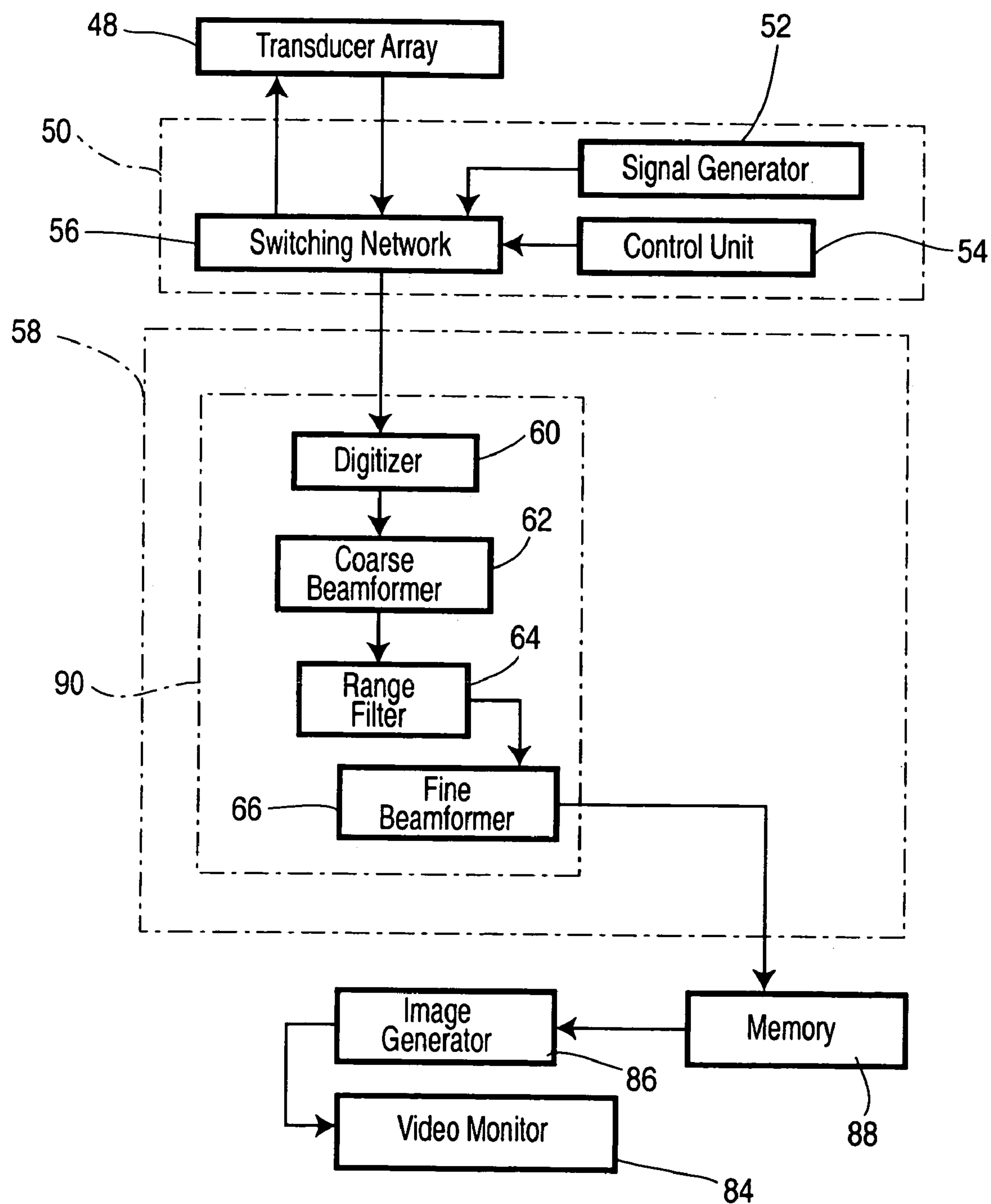
FIG. 6 is a block diagram showing functional components of an ultrasound scanning system in accordance with the present invention.

As illustrated in FIG. 6, a two-dimensional array 48 of transducer elements mounted to a probe (not shown in FIG. 6) is accessed by switching electronics 50. Switching electronics 50 includes a signal generator 52, a control unit 54 and a switching network 56. Signal generator 52 produces a waveform having a characteristic ultrasound frequency that is directed to elements of transducer array 48 by switching network 56 in response to signals from control unit 54. Switching electronics 50 selectively energizes the elements of array 48 and selectively polls those elements to effectively divide the array, along at least one of two dimensions, into subapertures 44$_a$, 44$_b$, . . . 44$_n$. As discussed above, each subaperture 44$_a$, 44$_b$, . . . 44$_n$ transmits and receives a respective plurality of low-resolution ultrasound beams 46$_{a1}$, 46$_{a2}$, . . . 46$_{ai}$, 46$_{b1}$, 46$_{b2}$, . . . 46b$_j$, . . . 46$_{n1}$, 46$_{n2}$, . . . 46$_{nk}$ that span the volume 42 to be imaged. A signal processor 58 is operatively coupled to the switching electronics 50 for coherently combining received beamformed signals from the subapertures 44$_a$, 44$_b$, . . . 44$_n$ and synthesizing, from the coherent combination, a large aperture focused at each point of the image volume 42.

The image formation process loops on beams 46$_{a1}$, 46$_{a2}$, . . . 46$_{ai}$, 46$_{b1}$, 46$_{b2}$, . . . 46b$_j$, . . . 46$_{n1}$, 46$_{n2}$, . . . 46$_{nk}$ and subapertures 44$_a$, 44$_b$, . . . 44$_n$ (2 nested loops), collecting range lines (the sampled signal in range). From each shot, return signals are received from the transducer elements of the transmitting/receiving subaperture 44$_a$, 44$_b$, . . . 44$_n$. These signals are digitized by a digitizer 60 (FIG. 6) and (coarse) beamformed by a module 62, with dynamic focussing along the radial line from the phase center of the subaperture through the transmit focal point, as is usually done.

In this preferred embodiment, the next operation performed on each line is range filtering, performed by a range filter 64. This operation is linear for the fine beamforming step to work optimally, and it retains the complex-valued nature of the signal; i.e. the output remains complex (I and Q). A conventional bandpass filter can be applied (matching the waveform bandwidth), or alternatively, a matched filter can be used and applied to the ultrasound signals; in this case, a preferred approach is to base the matched filter on the pulse replica (as the real part of the kernel) and its Hilbert transform (as the imaginary part). Matched filtering with the transmit pulse is logically done after coarse beamforming, but before fine beamforming, since fine beamforming (module 66) removes the range lines. Range filtering may also be omitted depending on the waveform used.

One advantage of the way coarse beamforming and range filtering is performed is that a 2D ultrasound engine could be used for these operations, making the preferred 2D probe and the CAC-BF method amenable for upgrading existing premium ultrasound systems.

The resulting coarse beams are transferred to the fine beamforming module 66. Coarse beamformer module 62 and fine beamformer module 66 may be realized by generic digital processor circuits modified by respective programming algorithms to accomplish the respective beamforming operations.

A conventional ultrasound also loops on beams in a similar manner, but our invention uses a unique set of different beams, differing in both the elements used and the focused directions. With conventional ultrasound, each image point is typically generated from the nearest high-resolution beam which is generated from one or more shots. With the CAC-BF method on the other hand, each image point is generated from an associated set of nearby low-resolution beams, each generated from an associated shot.

Coherent Aperture Combining Beamforming: Fine Beamforming

Figure 7:
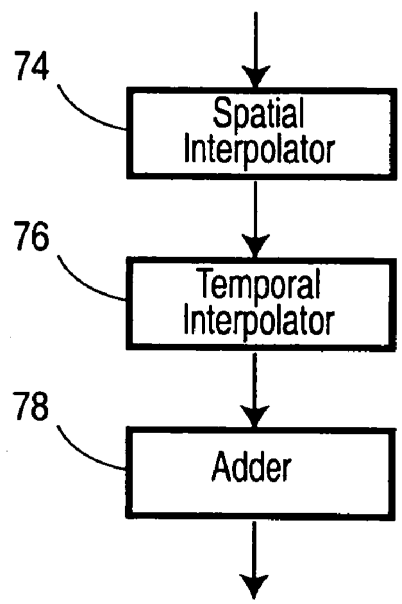
FIG. 7 is a block diagram showing elements of a fine beamformer shown in FIG. 6.
Figure 8:
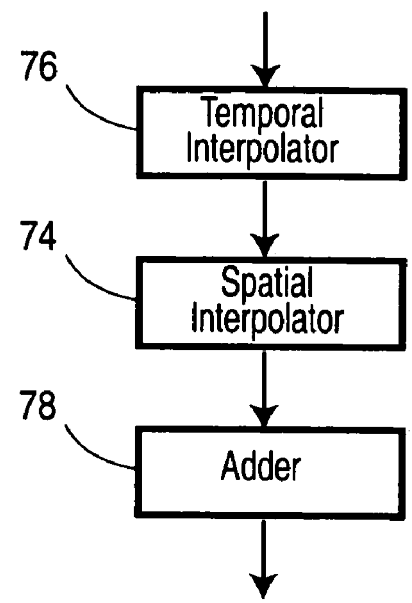
FIG. 8 is a block diagram similar to FIG. 7, showing an alternative configuration of the fine beamformer of FIG. 6.

The image space is divided into a high-resolution grid of voxels. The voxels are spaced more finely than the coarse beams $\mathbf{46}_{a1}$, $\mathbf{46}_{a2}$, . . . $\mathbf{46}_{ai}$, $\mathbf{46}_{b1}$, $\mathbf{46}_{b2}$, . . . 46b$_j$, . . . $\mathbf{46}_{n1}$, $\mathbf{46}_{n2}$, . . . $\mathbf{46}_{nk}$, nominally at the achievable resolution in cross-range from the synthesized apertures. In FIG. 5B two beam boresights (range lines) $\mathbf{46}_{a1}$, $\mathbf{46}_{a2}$ and $\mathbf{46}_{b1}$, $\mathbf{46}_{b2}$ from each of two subapertures $\mathbf{44}_a$ and $\mathbf{44}_b$, along with four grid points $\mathbf{72}_a$, $\mathbf{72}_b$, $\mathbf{72}_c$, $\mathbf{72}_d$, are shown. The intensity at each image point (voxel) $\mathbf{72}_a$, $\mathbf{72}_b$, $\mathbf{72}_c$, $\mathbf{72}_d$ is the coherent sum of signals received from the various nearby subaperture-beam shots. The sum is from subapertures across the array, thereby synthesizing a larger, composite aperture. From a given subaperture, each voxel's sum preferably includes the two nearest beams that straddle the given voxel $\mathbf{72}_a$, $\mathbf{72}_b$, $\mathbf{72}_c$, or $\mathbf{72}_d$. For example, for voxel $\mathbf{72}_d$ and subaperture $\mathbf{44}_a$, the two beams $\mathbf{46}_{a1}$ and $\mathbf{46}_{a2}$ are used. More particularly, signal sample points 73 and 73' are used. The spatial interpolation weight for each of the two beams is such that the pattern of the interpolated beam reaches a maximum (peaks) at the voxel. For image points between the beams, this not only helps the signal-to-noise ratio, but it also reduces the sidelobe pattern of the interpolated beam. Time-interpolation of the signal sample from each shot is also preferably included in the summation at each voxel, as illustrated in FIG. 5B. Various methods for spatial and temporal interpolation known to those skilled in the art all fall within the scope of the fine beamforming method, as does using a different number of beams or time samples for interpolation. FIGS. 7 and 8 illustrate possible modular combinations of a spatial interpolator 74, a temporal interpolator 76, and an adder 78. The result of applying the aforementioned fine beamforming algorithm is that the signal samples from a scatterer at the voxel all peak and add up in phase when summed. The range delay (which determines the phase) for a given voxel's signal sample is equal to the range delay between the subaperture phase center and the voxel. Line 68 (FIG. 5B) represents points with approximately the same range delay to voxel $\mathbf{72}_d$ from subaperture $\mathbf{44}_a$ and line 70 represents points with approximately the same range delay to voxel $\mathbf{72}_d$ from subaperture $\mathbf{44}_b$.

Figure 9:
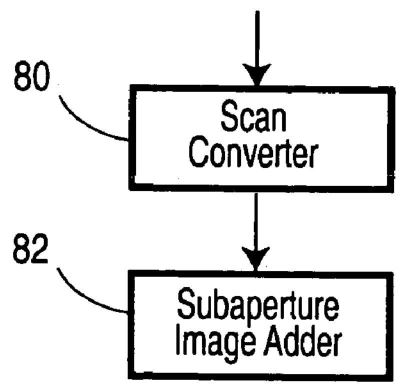
FIG. 9 is a block diagram similar to FIGS. 7 and 8, showing another alternative configuration of the fine beamformer of FIG. 6.

Another preferred embodiment of the fine beamforming algorithm is depicted schematically in FIG. 9. The coarse-resolution range lines from each subaperture $\mathbf{44}_a$, $\mathbf{44}_b$, . . . $\mathbf{44}_n$ are scan-converted by a module 80 (using conventional scan conversion algorithms known to those skilled in the art) to the high-resolution Cartesian grid of voxels to form a low-resolution subaperture image. In this operation, the complex nature of the signal (amplitude and phase) are retained. The subaperture images are added together by a module 82 to synthesize a larger aperture, and result in the final, high-resolution image. This addition operation can be with unity weights, or alternatively, non-unity weights to effect a taper. One advantage of this embodiment is that low-resolution images can be created quickly at a high frame rate. Higher and higher-resolution images can be obtained by using more and more subapertures and combining their respective low-resolution images.

The high-resolution image, once formed using CAC-BF as described above, can be further processed and/or transformed using image processing methods known to those skilled in the art. The image can be rectified (i.e. converted to an amplitude or power) or its real and/or imaginary parts can be processed.

A key advantage of using a CAC-BF approach is that high-resolution beams are obtained in less time for given number of (element) channels. This advantage is demonstrated in the discussion that follows.

A problem with conventional ultrasound beamforming, when applied to 2D scanning, is that it can take multiple (synthetic aperture) shots to form a high-resolution beam. This happens when the beam requires more elements than there are channels. This can make acquisition time unwieldy, especially for 3D ultrasound. For example, it takes at least 52 seconds to image a volume of 25.6 mm by 25.6 mm by 7 cm using λ-spaced elements in azimuth and elevation; and at least 13 seconds when 4λ-elements rather than λ-sized are used in the elevation dimension, when only 128 channels are available. This assumes sequential scanning in both azimuth and elevation with a beam step of λ in azimuth and 2λ in elevation, and an F/4 elevation resolution.

Consider first the λ-spaced-element case in azimuth and elevation. In this case, in order to support the aforementioned undistorted volume with F/2 in azimuth and F/8 in elevation (F/4 in elevation results in an undistorted elevation volume dimension that is less than 25.6 mm), the array is 256λ by 160λ with 256 elements in azimuth and 160 in elevation, for a total of 40,960 elements. For F/4 and F/8 in elevation, the receive subaperture has 128×64=8,192 elements and 128×32=4,096 elements, respectively. The number of beams required to sample the volume is also 128×64=8,192 assuming a beam step of λ in azimuth and 2λ in elevation. Using a 10 kHz firing rate (suitable for 7 cm depth), the minimum acquisition time (i.e. with 1 shot per beam) is 0.8192 s, assuming that 8,192 receive channels and 4,096 receive channels are available, respectively, for F/4 and F/8 elevation resolution. Of course, building a system with these many channels is extremely expensive and impractical today. If only 128 channels are available (i.e. as found in modem premium systems), then at least 8,192 elements/128 channels=64 shots/beam and 4,096/128=32 shots/beam are needed, causing the acquisition times to increase to 52.4 s and 26.2 s, for F/4 and F/8 respectively. These numbers assume a single transmit focus. If multiple transmit focii are used (up to 4 are used in practice), then the acquisition times increase proportionately.

Consider next the case where 4λ-elements rather than λ-sized are used in the elevation dimension. Then the number of elevation elements per beam reduces to 16 and 8, for F/4 and F/8, respectively. As a result, the number of elements in each receive subaperture reduces to 2,048 and 1,024 respectively. If 2,048 and 1,024 receive channels are available for the respective F/4 and F/8 elevation resolutions, then the acquisition time is again 0.8192 s. With only 128 available channels, however, this acquisition time increases to 13.1 s and 6.55 s, respectively. Once again, these times increase proportionately with the number of transmit focii used.

With the present CAC-BF method, low-resolution beams $\mathbf{46}_{a1}$, $\mathbf{46}_{a2}$, . . . $\mathbf{46}_{ai}$, $\mathbf{46}_{b1}$, $\mathbf{46}_{b2}$, . . . $\mathbf{46}b_j$, . . . $\mathbf{46}_{n1}$, $\mathbf{46}_{n2}$, . . . $\mathbf{46}_{nk}$ are used, needing fewer elements per beam, so that potentially only one shot is needed per beam. The low-resolution beams $\mathbf{46}_{a1}$, $\mathbf{46}_{a2}$, . . . $\mathbf{46}_{ai}$, $\mathbf{46}_{b1}$, $\mathbf{46}_{b2}$, . . . $\mathbf{46}b_j$, . . . $\mathbf{46}_{n1}$, $\mathbf{46}_{n2}$, . . . $\mathbf{46}_{nk}$ cover a greater volume, but beams are needed from more (smaller) subapertures $\mathbf{44}_a$, $\mathbf{44}_b$, . . . $\mathbf{44}_n$ in order to get resolution. The volume is covered by the 'product' of subapertures $\mathbf{44}_a$, $\mathbf{44}_b$, . . . $\mathbf{44}_n$ and beams $\mathbf{46}_{a1}$, $\mathbf{46}_{a2}$, . . . $\mathbf{46}_{ai}$, $\mathbf{46}_{b1}$, $\mathbf{46}_{b2}$, . . . $\mathbf{46}b_j$, . . . $\mathbf{46}_{n1}$, $\mathbf{46}_{n2}$, . . . $\mathbf{46}_{nk}$. This can be accomplished with many subapertures, and few beams per subaperture (coarse beams, few elements per beam), or with just a few subapertures, with many beams per (finer beams, many elements per beam) subaperture. The product of the two (the total number of beams) is, to first order, independent of subaperture size. Thus with the present method, a certain number of beams $\mathbf{46}_{a1}$, $\mathbf{46}_{a2}$, . . . $\mathbf{46}_{ai}$, $\mathbf{46}_{b1}$, $\mathbf{46}_{b2}$, . . . $\mathbf{46}b_j$, . . . $\mathbf{46}_{n1}$, $\mathbf{46}_{n2}$, . . . $\mathbf{46}_{nk}$ are required to cover a given volume at a given resolution, and coverage time is proportional to volume/resolution. Once the beams $\mathbf{46}_{a1}$, $\mathbf{46}_{a2}$, . . . $\mathbf{46}_{ai}$, $\mathbf{46}_{b1}$, $\mathbf{46}_{b2}$, . . . $\mathbf{46}b_j$, . . . $\mathbf{46}_{n1}$, $\mathbf{46}_{n2}$, . . . $\mathbf{46}_{nk}$ are low enough resolution (i.e. they have a small enough number of elements), they only need one shot. Thus one of the key advantages of our method: when down to 1 shot for each beam, we have minimized coverage time. The aforementioned volume can now be imaged in under 1.6 seconds for F/4 in elevation, and in under 0.7 seconds for F/8 in elevation. The calculations are illustrated below.

Consider first the F/4 elevation case with 4λ-elements. With 16 elements needed in elevation and 128 channels available, one preferred CAC-BF solution is to use a receive subaperture containing 8 elements in azimuth and 16 elements in elevation. Using 41 subapertures $\mathbf{44}_a$, $\mathbf{44}_b$, . . . $\mathbf{44}_n$ to span the 128 azimuth elements with a preferred overlap of 5 elements between adjacent subapertures (in azimuth), a preferred 6 beams can be used to cover the 25 mm in azimuth. As a result, the number of beams (shots) needed to acquire the whole volume is 6 (per subaperture)×41 (subapertures)×64 (elevation beams)=15,744, which translates to an acquisition time of 1.57 s. Again, we have assumed a beam step of 2λ in elevation. Furthermore, because of the large depth of focus associated with the CAC-BF technique, a single transmit focus should suffice for virtually all imaging applications. This results in eight times the frame rate over the conventional beamforming technique, even when only a single transmit focus is employed with conventional imaging.

Finally, consider the F/8 elevation case with 4λ-elements and 128 available channels. With only 8 elements needed in elevation for each receive subaperture, one preferred CAC-BF solution is to use a receive subaperture containing 16 elements in azimuth and 8 elements in elevation. With 20 subapertures overlapped by a preferred 10 elements in azimuth to span the entire 128, 10 beams are preferably needed by each subaperture to cover the 25 mm in azimuth. As a result, 10×20×64=12,800 shots are needed which translates to 1.28 s for acquisition. The CAC-BF technique results in five times the frame rate over the conventional beamforming technique, in this case, assuming the conventional beamformer uses a single transmit focus. If the elevation beam step was increased to 4λ, then the frame time would reduce to 0.64 s using CAC-BF.

One advantage of the present methodology is that the composite aperture size can be tailored to every grid point $\mathbf{72}_a$, $\mathbf{72}_b$, $\mathbf{72}_c$, $\mathbf{72}_d$ (FIG. 5B). The preferred algorithm (using all available intersecting beams) naturally uses more apertures (on both transmit and receive) for grid points at greater ranges. With this embodiment, azimuth resolution (in mm) is constant with range. In a conventional ultrasound, the number of elements making up the aperture is not allowed to grow beyond the number of available channels. In the case of the present invention, the effective synthesized or composite aperture can grow to the full size of the physical aperture, exceeding the number of available channels, to the extent limited by the element directivity and desired grating lobe performance.

Another advantage of the CAC beamforming algorithm is that it can be combined with other conventional scanning approaches so that certain parts of a volume to be imaged use CAC beamforming while other parts use conventional beamforming. For example, CAC beamforming could be applied only at further ranges where resolution degrades and conventional beamforming used elsewhere.

Another advantage of the methodology described herein is that better depth of field is obtained with lower resolution beams. This means that an equivalent 3D volume can be covered with fewer shots, or a greater volume can be covered with the same number of shots.

Yet another advantage of the methodology described herein is that better resolution is achieved with the same size aperture (because of the lack of cross-terms). Resolution is two times better than that of a receive-only aperture (i.e. a system that uses a significantly lower resolution transmit aperture), and 1.4 times better than that of a conventional beam using full apertures on transmit and receive. It is to be noted that the full aperture is not normally used on transmit because of the limited depth of field, thus CAC-BF gets almost twice the resolution of conventional systems using the same sized physical aperture. Analyses and experimental measurements show that CAC-BF with 50% overlap performs equivalently to a conventional synthetic aperture of twice its size.

Other variations to the CAC-BF method are described to illustrate the scope of the CAC-BF method in accordance with the present invention.

CAC-BF can be performed with an arbitrary amount of subaperture overlap, recognizing that the resulting image (beam) response characteristics (e.g. the sidelobe behavior including the presence of grating lobes) at an image point will be affected accordingly.

It is to be noted that CAC-BF can be done in two dimensions, or, alternatively, CAC-BF can be performed in one dimension and conventional scanning in the other. CAC-BF can also be used with one-dimensional (1.5D, 1.75D etc.) probes to increase the frame rate for a given number of channels. The frame rate is further improved by the fact that the depth of focus is greater, reducing the number of transmit focii needed. Alternatively, larger effective apertures (better resolution) can be realized without reducing the frame rate. CAC-BF can also be used and tailored to work with systems having virtually any number of receive signal channels.

It is to be noted also that the fine grid within the image space need not be Cartesian and that the coarse beams need not be spaced equally in angle. For example, the beams could be spaced equally in sine-space, or spaced equally in the Cartesian grid. When CAC-BF is applied in both dimensions, the coarse beams could be placed on a grid that is not the product of an azimuth and an elevation grid (e.g. hexagonal or cylindrical scanning).

It is possible to include subaperture cross-terms, in order to improve sidelobes. Moreover, it is possible to transmit from one subaperture only, and receive from the rest of the subapertures.

This has the disadvantage of only getting half the resolution per length of aperture, but gets equivalent resolution to CAC-BF per pulse, because aperture overlap is not needed. A potential advantage is a reduction in hardware complexity (may not need transmit multiplexer, or it will be simpler). The reciprocal arrangement (transmit from all subapertures, only receive from middle one) may also be attractive.

Interpolation between beams helps reduce the sidelobes at grid points where the beams from different subapertures don't line up, effectively smoothing the addition of the subapertures at these points. The interpolation can be of any desired amount, using any algorithm known to those skilled in the art. It is possible not to use any interpolation but performance will be affected accordingly.

Shading (windowing) may be done in the summation across the aperture (to reduce sidelobes with narrow-band systems). For similar reasons, or alternatively, the subapertures themselves could be shaded or windowed.

Higher resolution coarse beams (requiring multiple shots) could be utilized, trading off coverage time versus sidelobes. Dynamic focussing may be unnecessary if beams are of low enough resolution (i.e. very small subapertures), and this may reduce complexity.

The 'product' of beams and subapertures need not have each of the nominally 50% overlapping subapertures transmitting all of the coarse beam angles. The product could be formed with a greater number of highly-overlapped subapertures, each transmitting a smaller number (e.g. one) of the beam angles. This has the advantage of having smaller blind zones at the close ranges between the subaperture centres, where no beams are transmitted.

Non-linear or adaptive, high-resolution beamforming techniques are computationally expensive, but may be worthwhile in some applications to combine the multiple subapertures used in the fine beamforming algorithm. The structure of the CAC-BF method is appropriate as there is typically a small number of subapertures. This is not burdensome if it takes a few seconds or minutes to compute; a physician could look at a linearly beamformed image, and suggest an area he would like to see better resolved; then the high-resolution algorithm could be applied.

Coherent Aperture Combining Beamforming: 2D Scanning

With 2D electronic scanning, the designer has a number of choices for which methods to use in each dimension. The choices include element size (n*lambda, where n can be between 0.5 and 4), what type of scanning (phased, sequenced, CAC-BF), the number of elements in the aperture, and with CAC-BF, the subaperture sizes and overlap. As element size goes up, the cost to achieve a certain level of resolution goes down, but sidelobe performance degrades. Each element size has a maximum achievable resolution, and larger elements have poorer performance. For example, 4-lambda elements cannot do better than about 0.35 mm azimuth resolution, whereas lambda elements can achieve about 0.2 mm azimuth resolution at 7.5 MHz. Systems using CAC-BF in 2D with lambda or 2-lambda elements in both dimensions are viable compromises. With CAC-BF, the larger the subapertures, the costlier (i.e. more channels are needed), but sidelobe performance is better. Once the 1D performance of each alternative is established by testing, then 2D cost/performance/acquisition-time trade-offs can begin. A key feature of the CAC-BF algorithm is that it naturally provides the designer with this cost/performance/acquisition time trade-off.

With 2D CAC-BF, in order to deal with motion within the imaged volume, one can transmit the beams ordered within the volume, i.e. all the beams in top left corner first, then each row left to right, rows ordered top to bottom. In this way, each grid point is illuminated over a short period of time. This is exactly true only in focal plane, grid points at longer or shorter ranges taking somewhat longer to illuminate. The alternative of ordering by subaperture means that every grid point requires the whole sequence of pulses to be imaged.

The CAC-BF method has been simulated extensively and its performance as described herein validated by these simulations. In addition, experimental results have been obtained by applying CAC-BF in the azimuth dimension as described herein using a 64-channel ultrasound system and a 192-element off-the-shelf probe, suitably programmed to implement the CAC-BF method. The improved resolution, the high-quality imagery, and the reduction in acquisition time compared to conventional beamforming have all been confirmed. Images (2D or 3D) may be generated on a video monitor 84 (FIG. 6) by an image generator 86 in response to image data stored in a memory 88 connected to output of processor 58, more particularly to an output of a CAC component 90, and even more particularly to an output of fine beamformer 66. CAC component 90 includes digitizer 60, coarse beamformer 62, range filter 64 and fine beamformer 66.

3D Ultrasound Imaging Systems

An ultrasound imaging system in accordance with the present invention provides a novel solution for 3D ultrasound imaging that is affordable, and yet high-performing. Unlike other designs which degrade state-of-the-art imaging performance in order to reduce cost, the present solution maintains or exceeds state-of-the-art imaging performance, while keeping the 3D ultrasound system cost comparable to that of 2D ultrasound systems.

State-of-the-art azimuth imaging performance requires an F number of 2; i.e. an F/2. The F number is the ratio of the focal range divided by the imaging aperture dimension. For example, an F/2 at 5 cm depth requires an instantaneous receive aperture of size 2.5 cm. The present probe is designed to provide an F/2, and an enhanced resolution of F/1 (i.e. twice as good as state-of-the-art).

State-of-the-art elevation imaging performance requires an F/8. The present probe provides a standard elevation resolution of about F/8 and is capable of providing an enhanced elevation resolution of F/4 (twice as good as state-of-the-art) or better.

For state-of-the-art resolutions in both azimuth and elevation, the 2D probe of the present invention (for 3D imaging) is able to acquire a 25 mm×25 mm×70 mm volume electronically in under 1 second; the same volume is acquired with enhanced resolutions (azimuth and elevation) in under 2 seconds. And these acquisition times are achievable when just 128 receive channels are available, keeping the number of channels (and hence cost) comparable to state-of-the-art ultrasound imaging systems (for 2D imaging).

This win-win (performance-cost) 3D imaging technology is made possible from the use of the beamforming techniques of the present invention that reduce acquisition time (i.e. the number of shots needed) when the number of received channels available is less than the number of elements in the imaging aperture. The beamforming techniques are referred to as coherent aperture combining beamforming (CAC-BF) as discussed earlier.

In order to reduce the element count and simplify the transducer design, the 2D probe pursuant to the present invention is able to exploit 1.75D elemental technology, with λ spacing in azimuth, and 4λ spacing in elevation in one preferred embodiment. As a result, its baseline transducer requires only 10λ elements, 256(λ)×40(4λ)=10,240, in order to produce an undistorted volume extending 25.6 mm in azimuth and 25.6 mm in elevation. The beamforming is completely electronic (i.e. no mechanical lenses are used in elevation). Individual receive beams use just 128×8=1,024 elements for standard, state-of-the-art imaging resolutions, and 128×16=2,048 elements for enhanced resolution imaging.

The 2D probe can be used with conventional beamforming algorithms, as well as with CAC-BF, making it very versatile, saving on the number of probes otherwise required by an ultrasound system. For example, it can operate as a conventional 1D array, employing conventional scanning techniques such as sequential or phased-array scanning in azimuth (or elevation) only. If 2D scanning is desired, then conventional electronic scanning can be performed in both azimuth and elevation. For example, if sequential beamforming is used in both azimuth and elevation, then for standard imaging resolutions (F/2 in azimuth and F/8 in elevation) 128 beams are needed in azimuth and 32 are needed in elevation to fill the volume. For the case of 70 cm depth, an acquisition time of 6.5 seconds results with two transmit focal ranges (128×32 vectors×8 shots/vector×2 focii/10 kHz). For enhanced imaging resolutions, 64 elevation beams are needed along with 16 shots/beam (2048 elements/128 channels) resulting in an acquisition time of 26.2 seconds.

With CAC-BF, the beamforming can be configured in a number of ways (as described earlier) to reduce the volume acquisition times required if only conventional beamforming algorithms were used. For standard imaging resolutions, consider the case where 20 overlapped subapertures, each consisting of 16 (in azimuth) by 8 (in elevation) elements are used with 10 shots (beams) per subaperture. CAC-BF is performed in azimuth while sequential beamforming is performed in elevation. The acquisition time for this configuration has already been shown to be just 0.64 seconds (10 shots/subap×20 subaps×32 elev_beams/10 kHz), a substantial reduction over the 6.5 seconds required using only sequential beamforming. For enhanced imaging resolutions, recall the case where 41 overlapped subapertures, each consisting of 8 (in azumith) by 16 (in elevation) elements are used with 6 shots (beams) per subaperture. In this case, the volume acquisition has been shown to take only 1.57 seconds (6 shots/subap×41 subaps×64 elev_beams/10 kHz), as compared to the 26.2 seconds needed by the sequential beamformer.

Although the invention has been described in terms of particular embodiments and applications, one of ordinary skill in the art, in light of this teaching, can generate additional embodiments and modifications without departing from the spirit of or exceeding the scope of the claimed invention. While the preferred embodiment described herein represents the form of the invention currently being developed for its carotid artery application, the scope of this invention goes far beyond the form of this preferred embodiment. For example, the CAC-BF solution can be used in the elevation dimension, instead of azimuth, or it could be used in both dimensions, and still be within the scope of the invention. Alternatively, the number and size of elements in each dimension of the transducer could be different, and still fall within the scope of the invention. In the limiting case, the 2D transducer array could collapse to be a 1D array (i.e. designed to scan in only one dimension), and if CAC-BF is used in that single dimension, this configuration is still within the scope of the invention. Accordingly, it is to be understood that the drawings and descriptions herein are proffered by way of example to facilitate comprehension of the invention and should not be construed to limit the scope thereof.

What is claimed is:

1. A system for gathering ultrasound image data in a scanning process, comprising:

a two-dimensional probe carrying a multiplicity of transducer elements disposed or arranged in an array in a first dimension and a second dimension of an image space;

switching electronics operatively connected to said probe for selectively energizing said transducer elements and selectively polling said transducer elements to effectively divide said array, along at least one of said first dimension and said second dimension, into a plurality of subapertures each transmitting and receiving a plurality of coarse or low-resolution ultrasound beams beamformed signals, the beamformed signals of said subapertures collectively spanning a volume to be imaged, said subapertures each having a length dimension or size and said beamformed signals each having a beam width or spatial resolution inversely related to the length dimension or size of the respective subaperture; and a signal processor operatively coupled to said switching electronics for coherently combining received low-resolution beamformed signals from said subapertures to synthesize a composite aperture having a larger length dimension or size than any one of said subapertures and focused at each point of said volume, resulting in image data at each point of said volume having higher a spatial resolution finer than the spatial resolution of any one of said beamformed signals in accordance with the larger length dimension or size of said composite aperture.

2. The system defined in claim 1 wherein said signal processor includes means for processing received signals from said subapertures to form said beamformed signals.

3. The system defined in claim 2 wherein said signal processor includes a coarse beamformer and a fine beamformer.

4. The system defined in claim 3 wherein said fine beamformer includes a spatial interpolator between beams.

5. The system defined in claim 3 wherein said fine beamformer includes a temporal interpolator along range lines.

6. The system defined in claim 3 wherein said fine beamformer includes a scan-converter for scan-converting range lines to a high-resolution grid of voxels to form a low-resolution subaperture image for each subaperture and further includes means for forming a coherent combination of the low-resolution subaperture images to synthesize a larger aperture and a final high-resolution image.

7. The system defined in claim 3 wherein said signal processor includes a range filter, the processing of received signals from said subapertures further including operating said range filter on coarse beamformed signals from said coarse beamformer prior to feeding of the coarse beamformed signals to said fine beamformer.

8. The system defined in claim 1 wherein said probe is driven by a waveform having an acoustic wavelength lambda corresponding to a center frequency corresponding to a characteristic wavelength of said waveform, said transducer elements having a first element size in said first dimension and a second element size in said second dimension, at least one of said first element size and said second element size being greater than or equal to twice said characteristic wavelength lambda.

9. The system defined in claim 8 wherein said first dimension and said second dimension are an azimuth dimension and an elevation dimension, respectively.

10. The system defined in claim 1 wherein said switching electronics includes a control unit ensuring that each subaperture transmits and receives a respective sequence of overlapping phased-array beams each focused at a different angle.

11. The system defined in claim 10 wherein said overlapping phased-array beams are spaced so as to cross approximately at respective −3 dB points.

12. The system defined in claim 10 wherein said transducer elements have an inter-element spacing, the overlapping beams of any given one of said subapertures subtending a total angle of less than a weighted mathematical reciprocal of said inter-element spacing.

13. The system defined in claim 1 wherein each of said subapertures overlaps an adjacent one of said subapertures, the overlap including at least 50% of the transducer elements included in said adjacent one of said subapertures.

14. The system defined in claim 1 wherein said subapertures extend along at least one of said first dimension and said second dimension.

15. The system defined in claim 1 wherein each of said subapertures is a source of an outgoing waveform.

16. The system defined in claim 1 wherein each of at least one said subapertures is a source of a plurality of low-resolution ultrasound beams that span the volume to be imaged.

17. The system defined in claim 1 wherein each of said subapertures is controlled by said switching electronics and said signal processor to generate a set of beamformed signals effectively encoding a respective coarse or low-resolution image of at least a portion of said volume to be imaged, said signal processor being operatively coupled to said switching electronics for coherently combining the beamformed signals from said subapertures to synthesize a high-resolution image spanning said volume to be imaged.

18. The system defined in claim 1 wherein, for each of said beamformed signals, a respective one of said subapertures is used for both transmitting and receiving.

19. The system defined in claim 1 wherein each of said beamformed signals is formed by selectively energizing and selectively polling only transducers in a single respective one of said subapertures.

20. The system defined in claim 1 wherein said switching electronics is operatively connected to said probe for selectively energizing said transducer elements and selectively polling said transducer elements so. that each given one of said subapertures receives only echo signals generated in response to signals transmitted by said given one of said subapertures, whereby each of said subapertures is used for both transmitting and receiving in generating the respective coarse or low-resolution ultrasound beamformed signals.

21. A system for gathering ultrasound image data in a scanning process, comprising:

a two-dimensional probe carrying a multiplicity of transducer elements disposed or arranged in an array in a first dimension and a second dimension of an image space;

switching electronics operatively connected to said probe for selectively energizing said transducer elements and selectively polling said transducer elements to effectively divide said array, along at least one of said first dimension and said second dimension, into a plurality of subapertures each transmitting and receiving a plurality of coarse or low-resolution ultrasound beams beamformed signals, the beamformed signals of said subapertures collectively spanning a volume to be imaged, said subapertures each having a length dimension or size and said beamformed signals each having a beam width or spatial resolution inversely related to the length dimension or size of the respective subaperture, each of said subapertures corresponding to a respective subset of said transducer elements, at least 50% of the transducer elements of each said subset being included in at least one other subaperture's subset of said transducer elements; and a signal processor operatively coupled to said switching electronics for coherently combining received low-resolution beamformed signals from said subapertures to synthesize a composite aperture having a larger length dimension or size than any one of said subapertures and focused at each point of said volume, resulting in image data at each point of said volume having higher a spatial resolution finer than the spatial resolution of any one of said beamformed signals in accordance with the larger length dimension or size of said composite aperture.

22. The system defined in claim 21 wherein said switching electronics are operatively connected to said probe for selectively energizing said transducer elements and selectively polling said transducer elements so that each given one of said subapertures receives only echo signals generated in response to signals transmitted by said given one of said subapertures, whereby each of said subapertures is used for both transmitting and receiving coarse or low-resolution ultrasound beams that span a volume to be imaged beamformed signals.

23. The system defined in claim 21 wherein each of said subapertures is controlled by said switching electronics and said signal processor to generate a set of beamformed signals effectively encoding a respective low-resolution image of at least a portion of said volume to be imaged, said signal processor being operatively coupled to said switching electronics for coherently combining the beamformed signals from said subapertures to synthesize a high-resolution image spanning said volume to be imaged.

24. The system defined in claim 21 wherein said signal processor includes means for processing received signals from said subapertures to form said beamformed signals.

25. The system defined in claim 24 wherein said signal processor includes a coarse beamformer and a fine beamformer.

26. A system for gathering ultrasound image data in a scanning process, comprising:

a two-dimensional probe carrying a multiplicity of transducer elements disposed or arranged in an array in a first dimension and a second dimension of an image space;

switching electronics operatively connected to said probe for selectively energizing said transducer elements and selectively polling said transducer elements to effectively divide said array, along at least one of said first dimension and said second dimension, into a plurality of subapertures each transmitting and receiving a plurality of coarse or low-resolution ultrasound beams beamformed signals, the beamformed signals of said subapertures collectively spanning a volume to be imaged, said subapertures each having a length dimension or size and said beamformed signals each having a beam width or spatial resolution inversely related to the length dimension or size of the respective subaperture, said switching electronics being operatively connected to said probe for selectively energizing said transducer elements and selectively polling said transducer elements so that each given one of said subapertures receives only echo signals generated in response to signals transmitted by said given one of said subapertures, whereby each of said subapertures is used for both transmitting and receiving in generating the respective coarse or low-resolution ultrasound beamformed signals; and a signal processor operatively coupled to said switching electronics for coherently combining received low-resolution beamformed signals from said subapertures to synthesize a composite aperture having a larger length dimension or size than any one of said subapertures and focused at each point of said volume, each of said subapertures being controlled by said switching electronics to generate a set of beamformed signals effectively encoding a respective coarse or low-resolution image of said volume to be imaged, said signal processor being operatively coupled to said switching electronics for coherently combining the beamformed signals from said subapertures to synthesize a high-resolution image spanning said volume to be imaged and having a spatial resolution finer than the spatial resolution of any one of said beamformed signals in accordance with the larger length dimension or size of said composite aperture.

27. The system defined in claim 26 wherein said signal processor includes means for processing received signals from said subapertures to form said beamformed signals.

28. The system defined in claim 27 wherein said signal processor includes a coarse beamformer and a fine beamformer.

29. A system for gathering ultrasound image data in a scanning process, comprising:

a two-dimensional probe carrying a multiplicity of transducer elements disposed or arranged in an array in a first dimension and a second dimension of an image space;

switching electronics operatively connected to said probe for selectively energizing said transducer elements and selectively polling said transducer elements to effectively divide said array, along at least one of said first dimension and said second dimension, into a plurality of subapertures each transmitting and receiving a plurality of coarse or low-resolution ultrasound beams beamformed signals, wherein for each of said beamformed signals, a respective one of said subapertures is used for both transmitting and receiving, the beamformed signals of said subapertures collectively spanning a volume to be imaged, said subapertures each having a length dimension or size and said beamformed signals each having a beam width or spatial resolution inversely related to the length dimension or size of the respective subaperture, at least one of said subapertures employing a plurality of low-resolution ultrasound beams beamformed signals different from a plurality of low-resolution ultrasound beams beamformed signals used by another of said subapertures; and a signal processor operatively coupled to said switching electronics for coherently combining received low-resolution beamformed signals from said subapertures to synthesize a composite aperture larger than any one of said subapertures and focused at each point of said volume, resulting in image data at each point of said volume having higher a spatial resolution finer than the spatial resolution of any one of said beamformed signals in accordance with the larger length dimension or size of said composite aperture.

30. A system for gathering ultrasound image data in a scanning process, comprising:

a two-dimensional probe carrying a multiplicity of transducer elements disposed or arranged in an array in a first dimension and a second dimension of an image space;

switching electronics operatively connected to said probe for selectively energizing said transducer elements and selectively polling said transducer elements to effectively divide said array, along at least one of said first dimension and said second dimension, into a plurality of subapertures each transmitting and receiving a plurality of coarse or low-resolution ultrasound beams beamformed signals, each of said beamformed signals being formed by selectively energizing and selectively polling only transducers in a single respective one of said subapertures, the beamformed signals of said subapertures collectively spanning a volume to be imaged, said subapertures each having a length dimension or size and said beamformed signals each having a beam width or spatial resolution inversely related to the length dimension or size of the respective subaperture; and a signal processor operatively coupled to said switching electronics for coherently combining received low-resolution beamformed signals from said subapertures to synthesize a plurality of composite apertures, each of said composite apertures being having a larger length dimension or size than every one of said subapertures and focused at a set of points of said volume, resulting in image data at each point of said volume having higher a spatial resolution finer than the spatial resolution of any one of said beamformed signals in accordance with the larger length dimension or size of a particular one of said composite apertures used for that point.

31. A system for gathering ultrasound image data in a scanning process, comprising:

a multiplicity of transducer elements arranged in an array;

switching electronics operatively connected to said array for selectively energizing said transducer elements and selectively polling said transducer elements to effectively divide said array, into a plurality of subapertures each transmitting and receiving a plurality of coarse or low-resolution ultrasound beams beamformed signals, each of said beamformed signals being formed by selectively energizing and selectively polling only transducers in a single respective one of said subapertures, the beamformed signals of said subapertures collectively spanning a region to be imaged, said subapertures each having a length dimension or size and said beamformed signals each having a beam width or spatial resolution inversely related to the length dimension or size of the respective subaperture; and a signal processor operatively coupled to said switching electronics for coherently combining received low-resolution beamformed signals from said subapertures to synthesize a composite aperture having a larger length dimension or size than any one of said subapertures and focused at each point of said region, resulting in image data at each point of said region having higher a spatial resolution finer than the spatial resolution of any one of said beamformed signals in accordance with the larger length dimension or size of said composite aperture.

32. The system defined in claim 31 wherein said transducer elements have an element size in a scanning dimension along said array, said element size being greater than half of an acoustic wavelength driving said transducer elements.

33. The system defined in claim 31 wherein at least one of said subapertures employs a plurality of coarse or low-resolution ultrasound beams beamformed signals different from a plurality of coarse or low-resolution ultrasound beams beamformed signals used by another of said subapertures.

34. The system defined in claim 31 wherein combining received beamformed signals from at least one of said subapertures to synthesize a larger aperture includes spatially interpolating said signals at points in said region.

35. The system defined in claim 31 wherein combining received beamformed signals includes weighting the signals from said subapertures to achieve improved sidelobe performance.

36. A system for gathering ultrasound image data in a scanning process, comprising:

an array of a multiplicity of transducer elements;

switching electronics operatively connected to said array for selectively energizing said transducer elements and selectively polling said transducer elements to effectively divide said array into a plurality of subapertures each transmitting and receiving a plurality of coarse or low-resolution ultrasound beams beamformed signals, wherein for each of said beamformed signals, a respective one of said subapertures is used for both transmitting and receiving, the beamformed signals of said subapertures collectively spanning a region to be imaged, said subapertures each having a length dimension or size and said beamformed signals each having a beam width or spatial resolution inversely related to the length dimension or size of the respective subaperture; and a signal processor operatively coupled to said switching electronics for coherently combining received low-resolution beamformed signals from sets of said subapertures to synthesize respective composite apertures, each given one of said composite apertures being having a larger length dimension or size than every one of the subapertures of the respective set of subapertures used to synthesize said given one of said composite apertures and being focused at a set of points of said region, resulting in image data at each point of said region having higher a spatial resolution finer than the spatial resolution of any one of said beamformed signals in accordance with the larger length dimension or size of a particular one of said composite apertures used for that point.

* * * * *